United States Patent
André et al.

(10) Patent No.: US 11,648,350 B2
(45) Date of Patent: May 16, 2023

(54) DRIVE UNIT FOR A MEDICAMENT DELIVERY DEVICE

(71) Applicant: SHL MEDICAL AG, Zug (CH)

(72) Inventors: Erika André, Saltsjö-Boo (SE); Anders Holmqvist, Värmdö (SE); Pär Leander, Nacka (SE); Linda Odelberg, Ekerö (SE)

(73) Assignee: SHL MEDICAL AG, Zug (CH)

( * ) Notice: Subject to any disclaimer, the term of this patent is extended or adjusted under 35 U.S.C. 154(b) by 128 days.

(21) Appl. No.: 16/649,334

(22) PCT Filed: Sep. 10, 2018

(86) PCT No.: PCT/EP2018/074237
§ 371 (c)(1),
(2) Date: Mar. 20, 2020

(87) PCT Pub. No.: WO2019/063267
PCT Pub. Date: Apr. 4, 2019

(65) Prior Publication Data
US 2020/0289753 A1    Sep. 17, 2020

(30) Foreign Application Priority Data

Sep. 28, 2017   (EP) .................................... 17193709

(51) Int. Cl.
*A61M 5/20*   (2006.01)
*A61M 5/315*  (2006.01)
*A61M 5/32*   (2006.01)

(52) U.S. Cl.
CPC ........ *A61M 5/2033* (2013.01); *A61M 5/3157* (2013.01); *A61M 5/3202* (2013.01);
(Continued)

(58) Field of Classification Search
CPC .............. A61M 5/2033; A61M 5/3157; A61M 2005/2073; A61M 2205/581;
(Continued)

(56) References Cited

U.S. PATENT DOCUMENTS

2011/0172640 A1*   7/2011   Cronenberg ...... A61M 5/31595
                                                              604/209
2013/0303985 A1*  11/2013   Wotton ............... A61M 5/2033
                                                              604/115
(Continued)

FOREIGN PATENT DOCUMENTS

EP   2340862 B1    7/2013
WO   2011/123024 A1   10/2011
(Continued)

OTHER PUBLICATIONS

International Search Report and Written Opinion for Int. App. No. PCT/EP2018/074237, dated Nov. 7, 2018.

*Primary Examiner* — Bhisma Mehta
*Assistant Examiner* — Nidah Hussain
(74) *Attorney, Agent, or Firm* — McDonnell Boehnen Hulbert & Berghoff LLP

(57) ABSTRACT

A drive unit for a medicament delivery device is presented having an elongated plunger rod extending in a longitudinal direction, a drive force element capable of applying a drive force on the elongated plunger rod, and an actuator operably connected to the elongated plunger rod for releasably holding the elongated plunger rod in an energized state when the drive force element is exerting a drive force on the elongated plunger rod. An activator is operably connected to the actuator for releasably holding the actuator in a holding position where the actuator is designed to be movable from the holding position in a direction generally transversal to
(Continued)

the longitudinal direction upon a displacement of the activator for releasing the plunger rod.

18 Claims, 32 Drawing Sheets

(52) U.S. Cl.
CPC .............. *A61M 2005/2073* (2013.01); *A61M 2205/581* (2013.01); *A61M 2205/582* (2013.01)

(58) Field of Classification Search
CPC .......... A61M 2205/582; A61M 5/3202; A61M 5/31576; A61M 5/315; A61M 5/31501; A61M 2005/31508
USPC ......................................................... 604/197
See application file for complete search history.

(56) References Cited

U.S. PATENT DOCUMENTS

2016/0193416 A1\* 7/2016 Olson ................. A61M 5/3158
  604/192
2016/0325047 A1\* 11/2016 Vedrine ............... A61M 5/3202

FOREIGN PATENT DOCUMENTS

| WO | 2016/202555 A1 | 12/2016 |
| WO | 2017/102175 A1 | 6/2017 |

\* cited by examiner

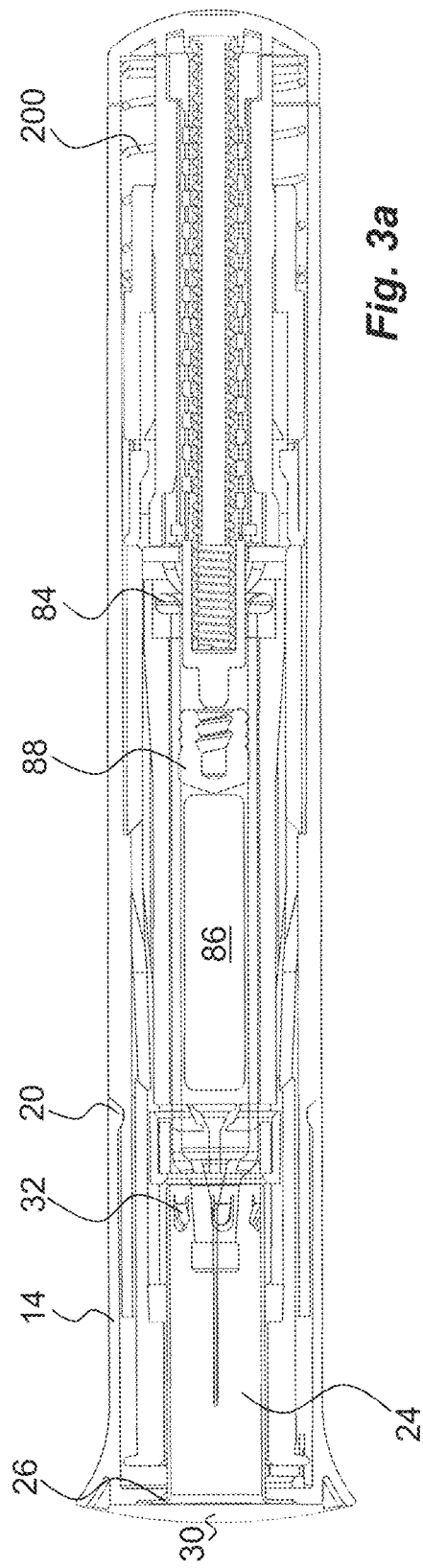
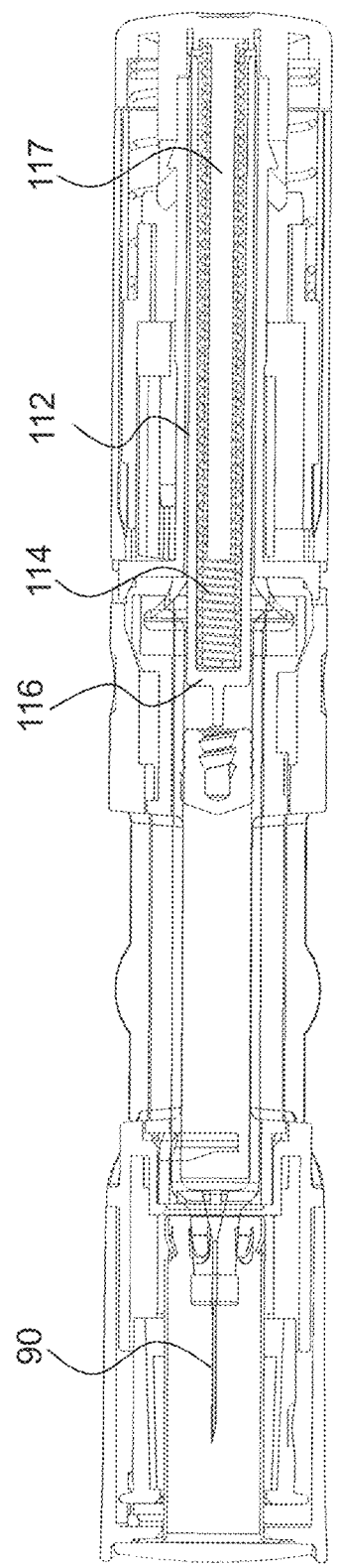
Fig. 3a
Fig. 3b

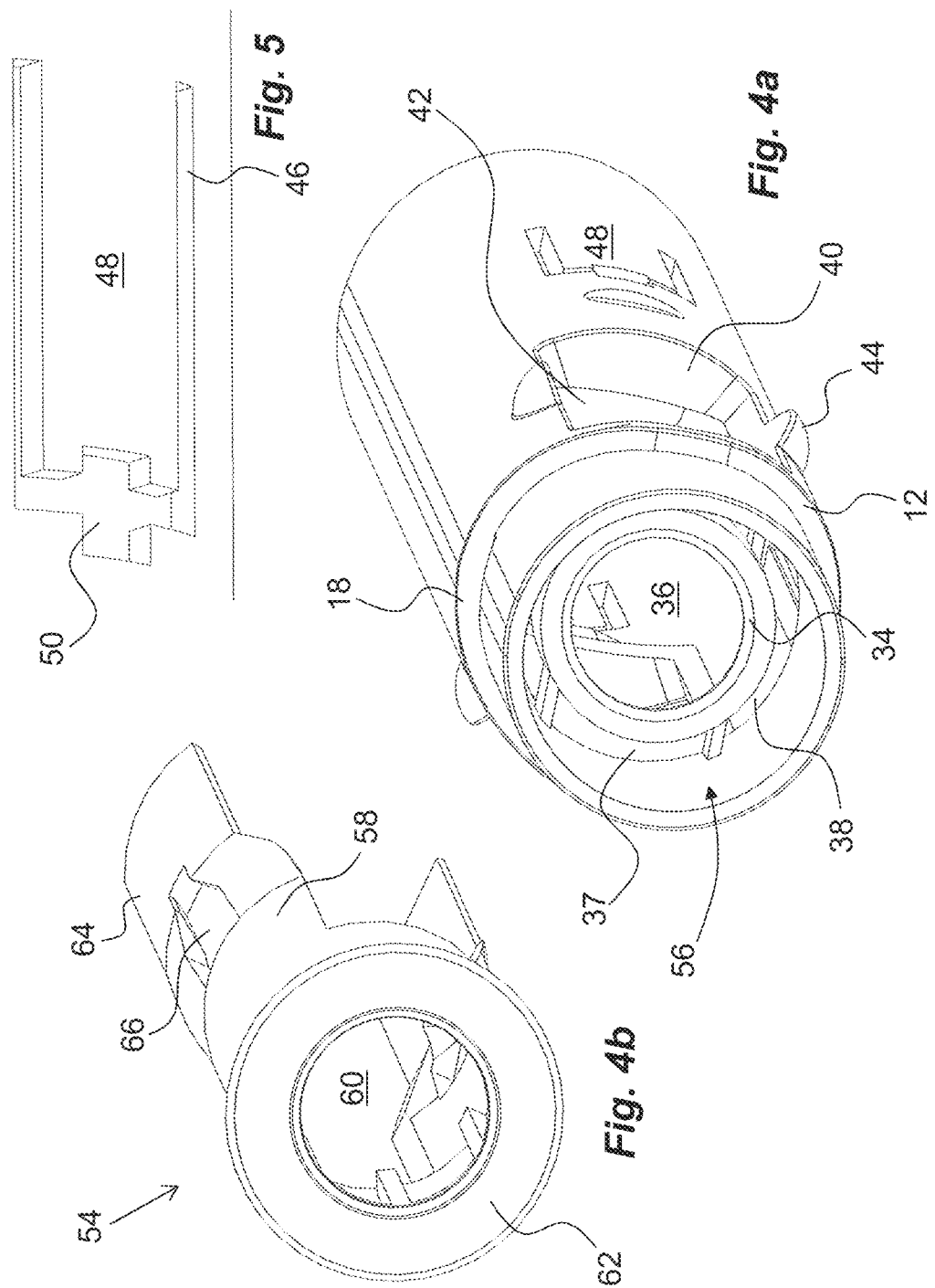

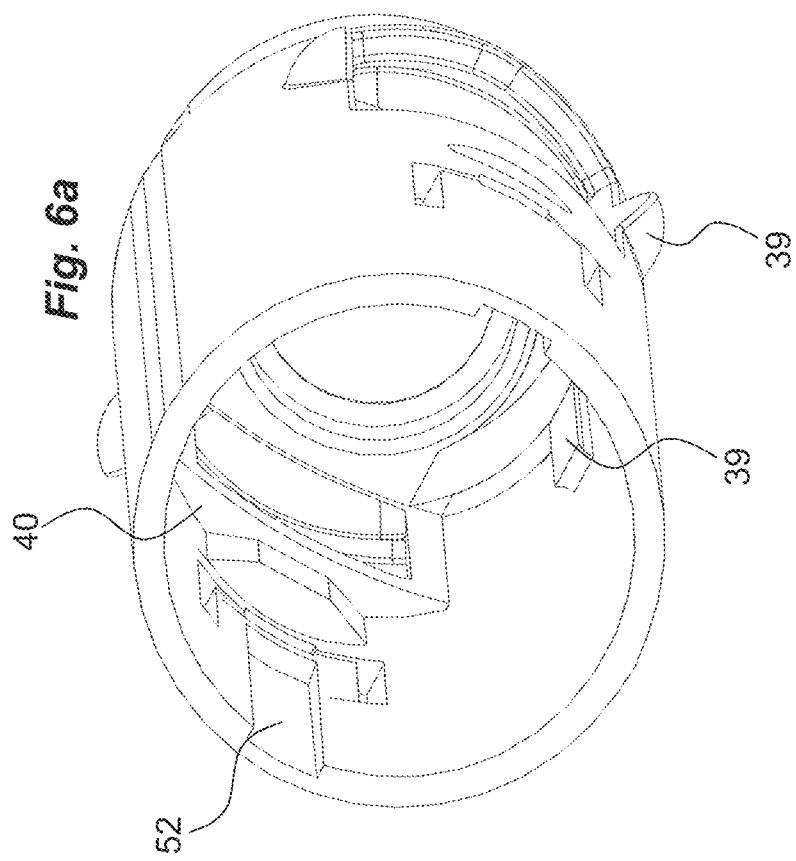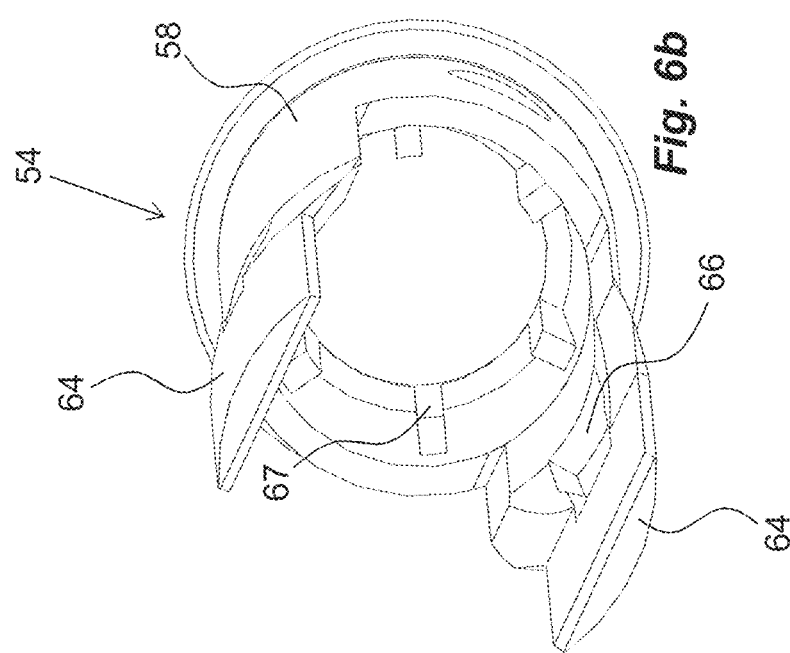

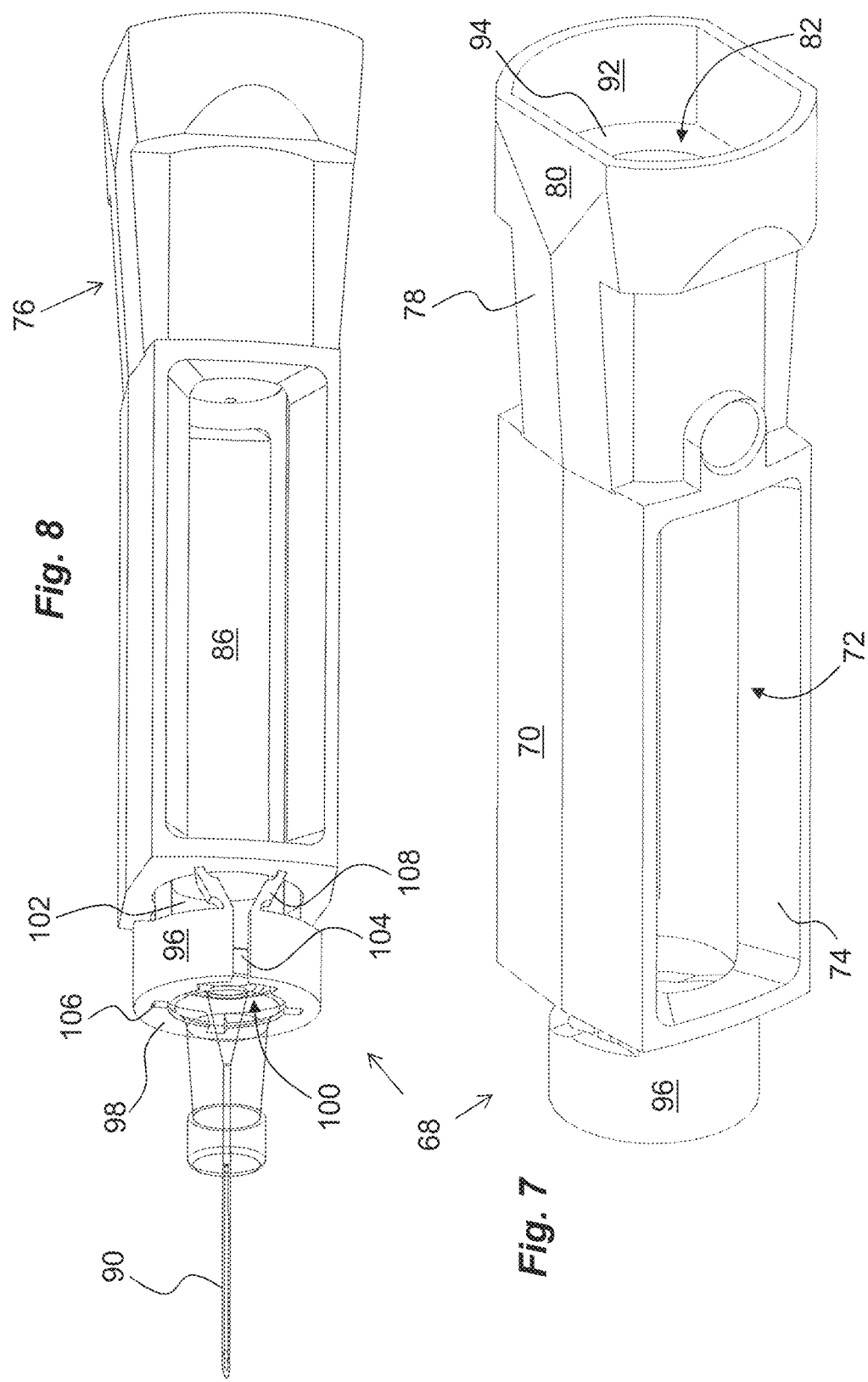

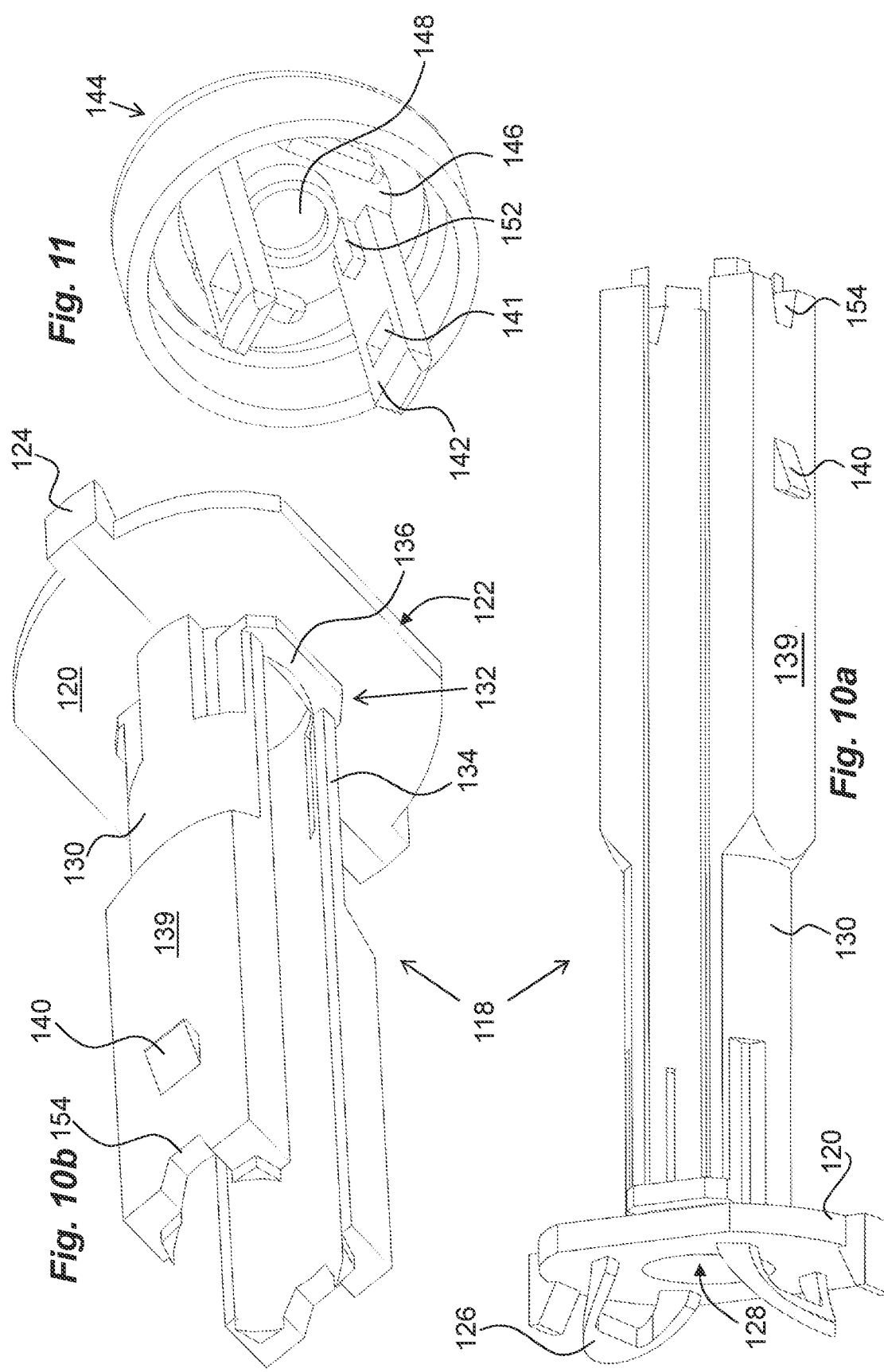

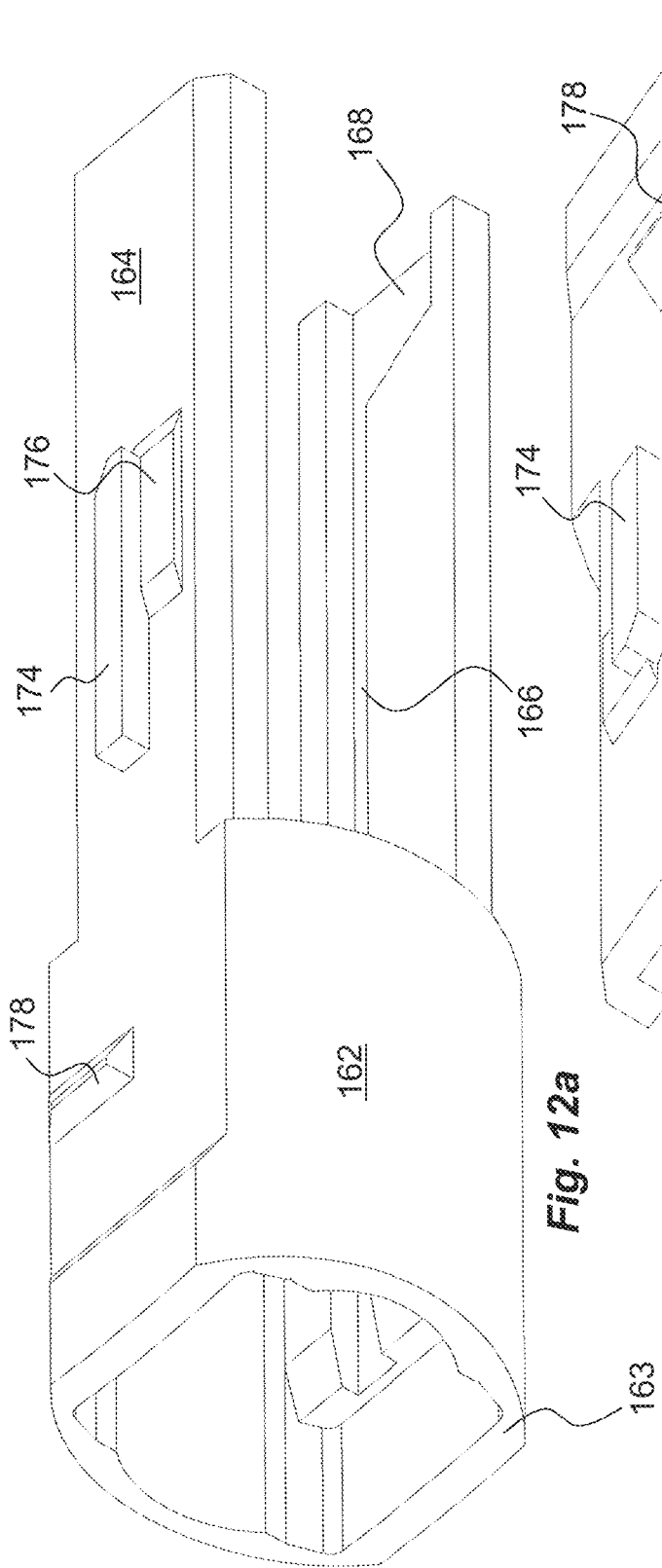
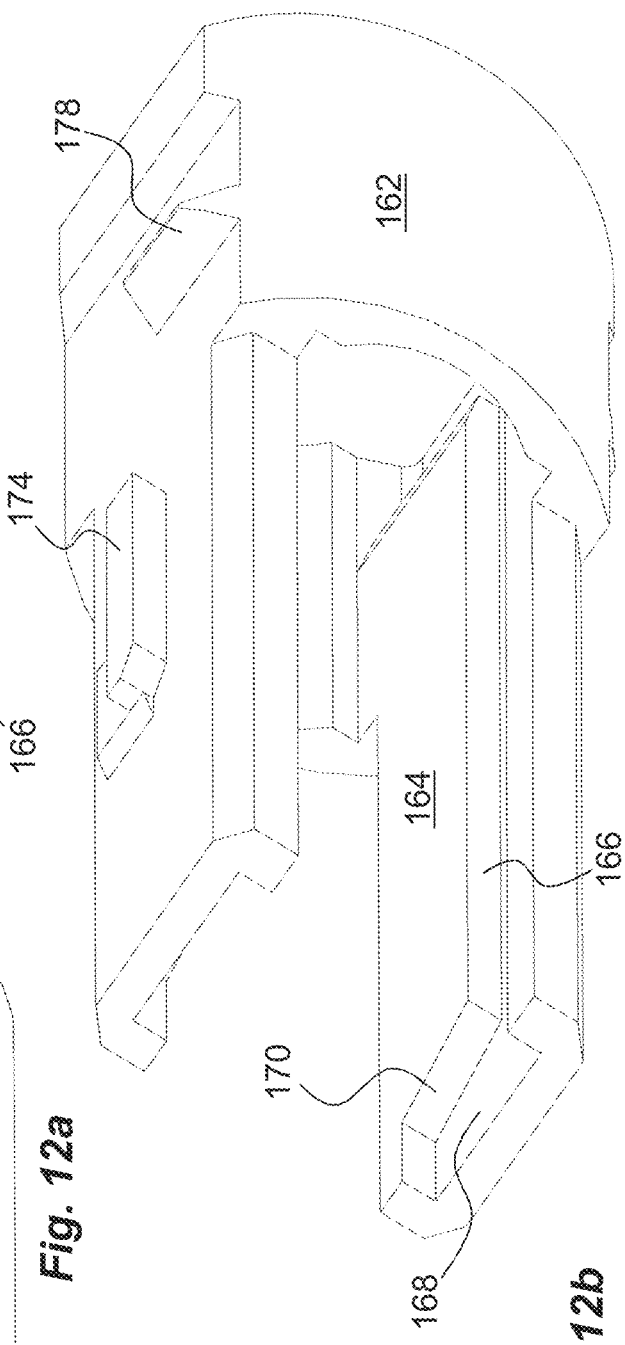

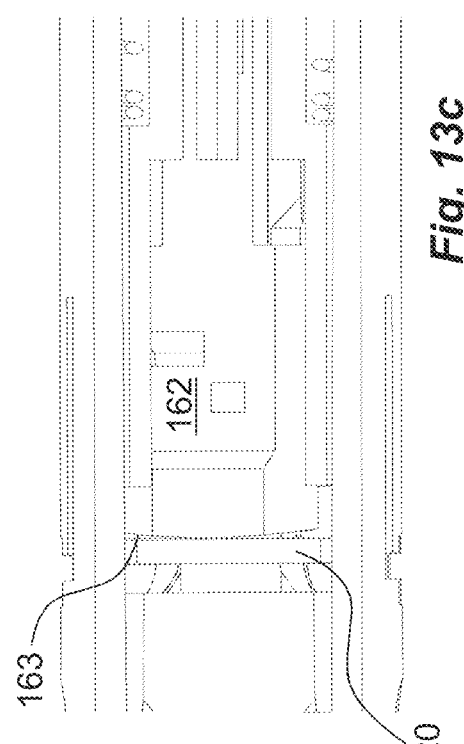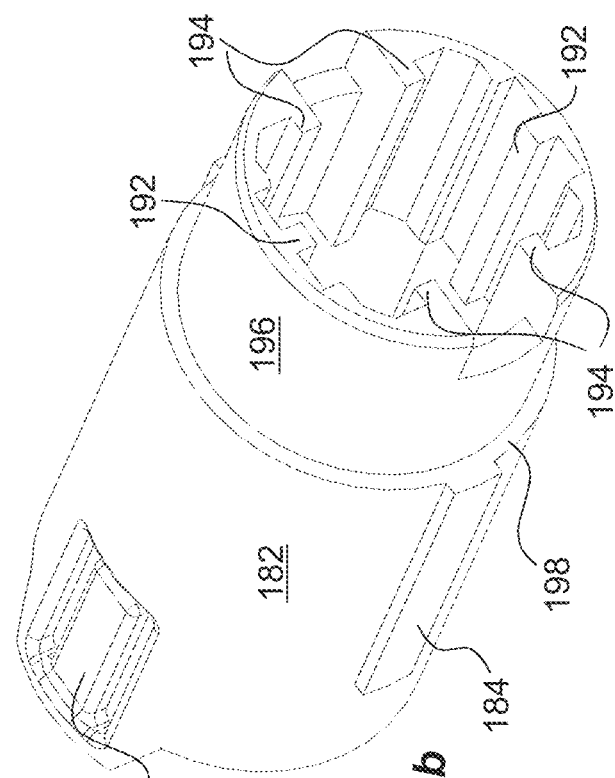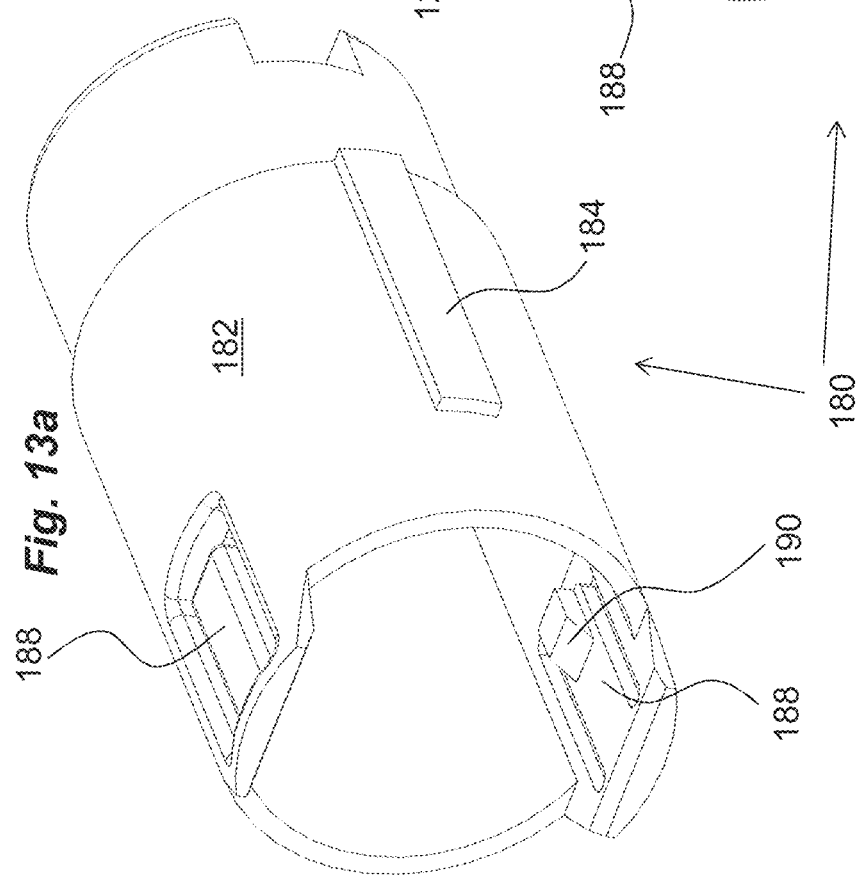

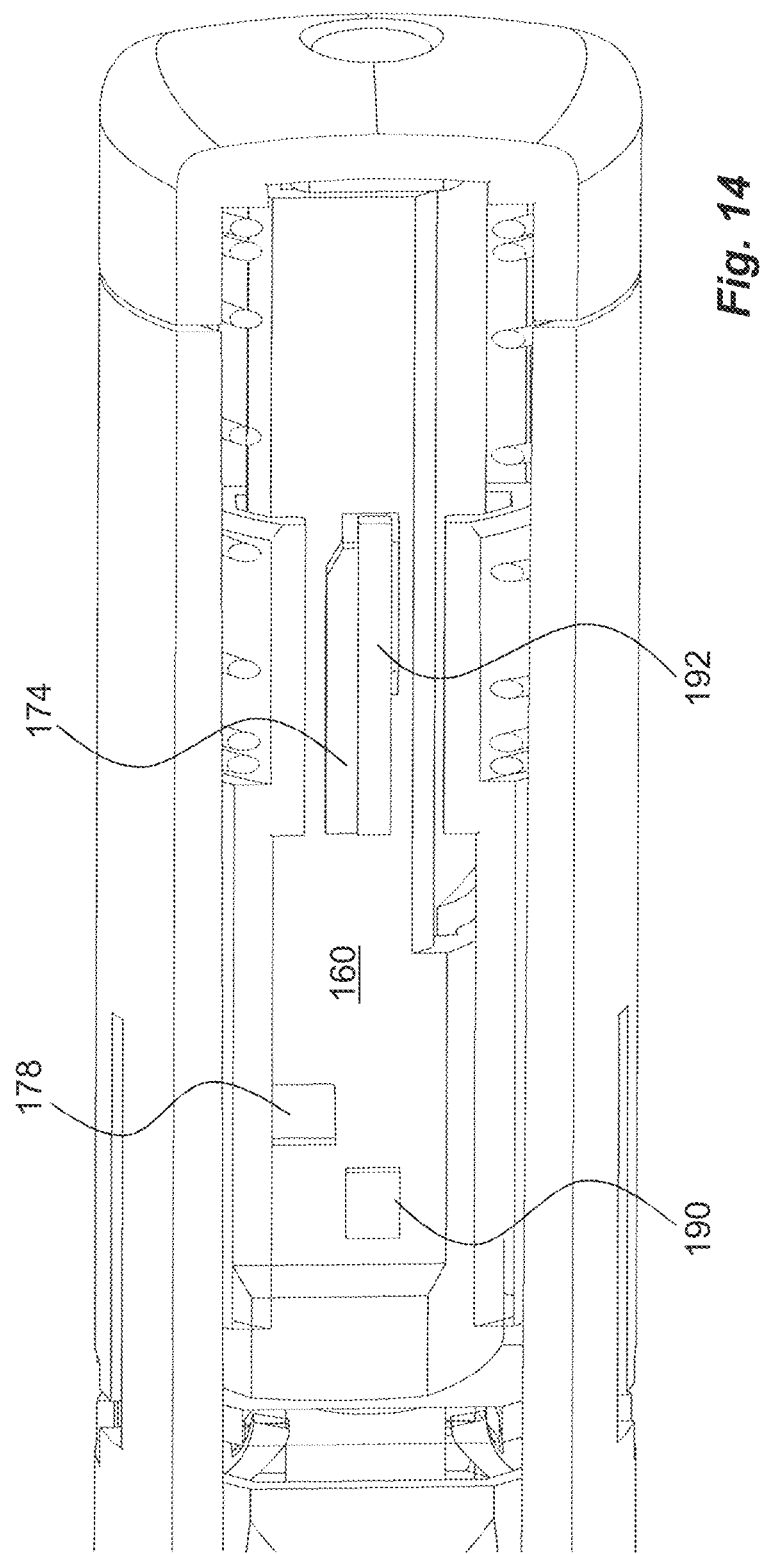

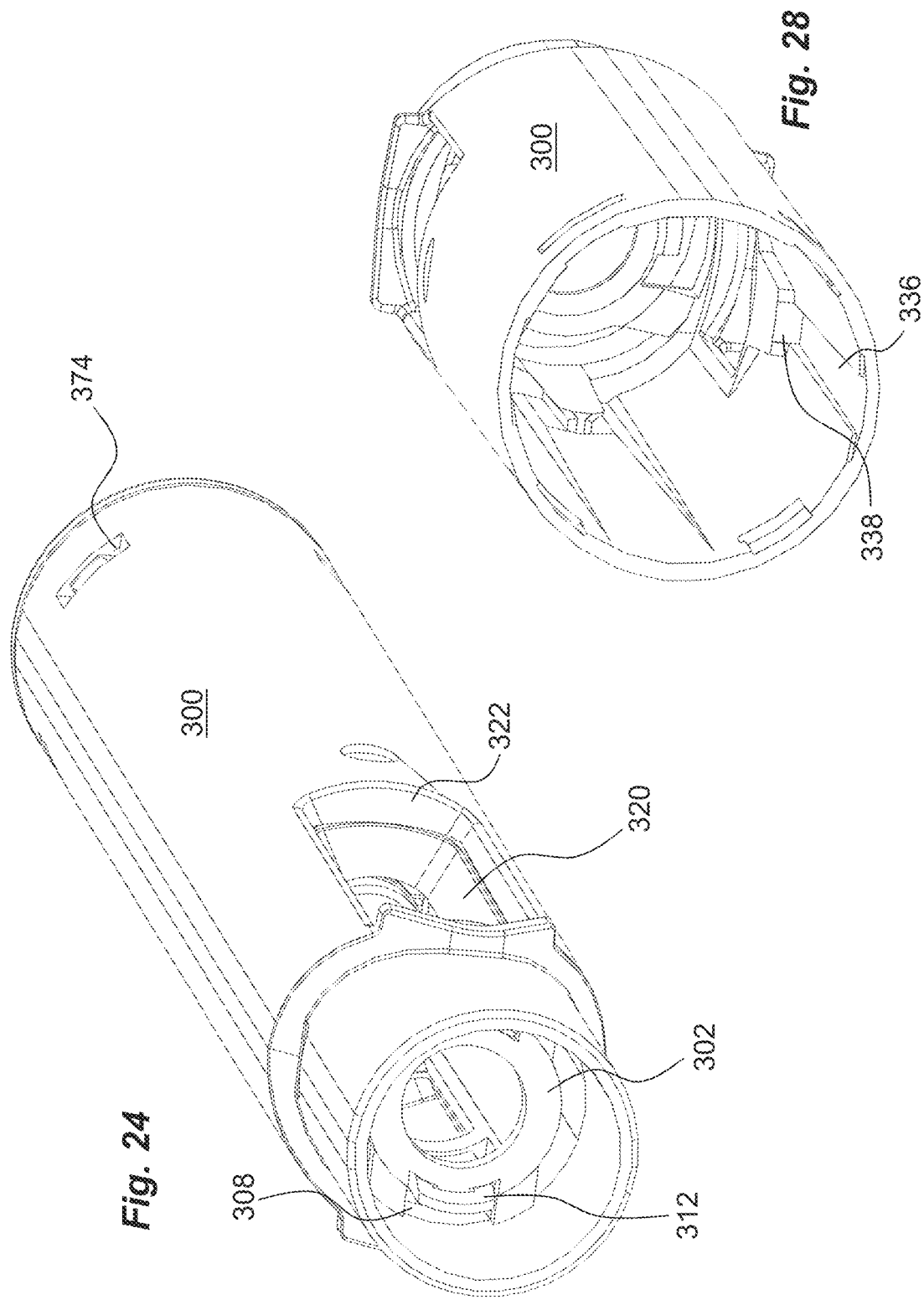

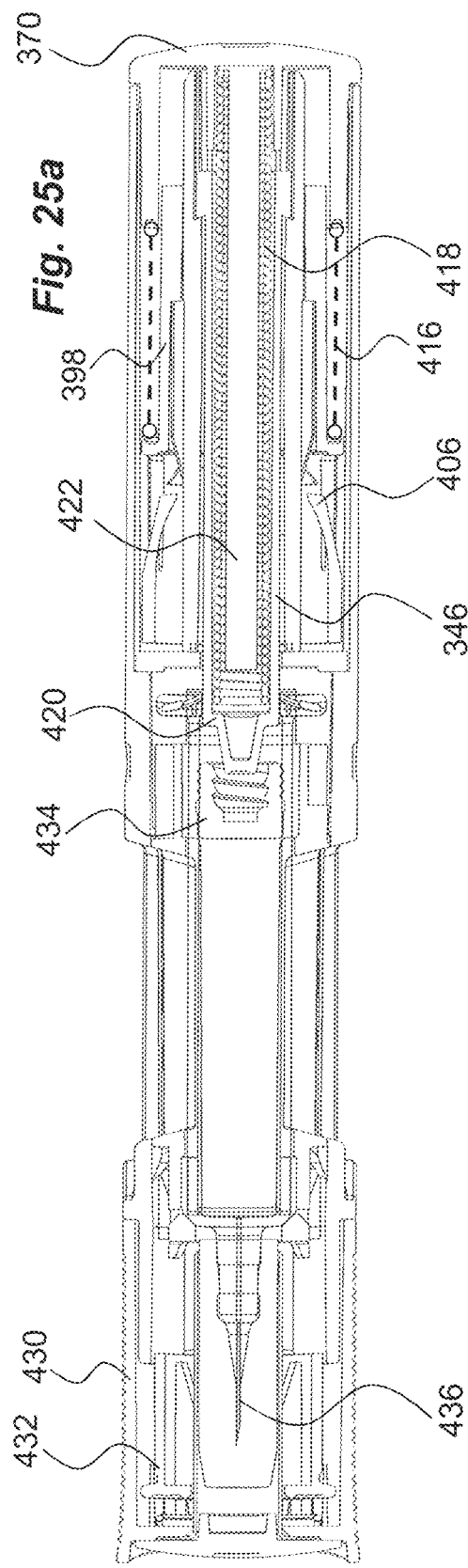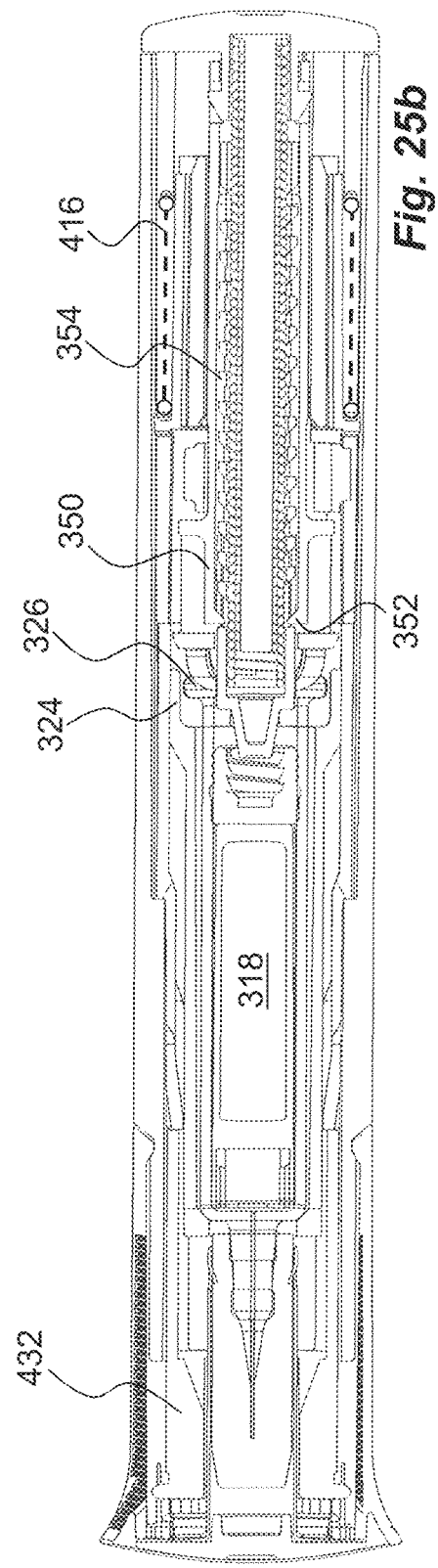

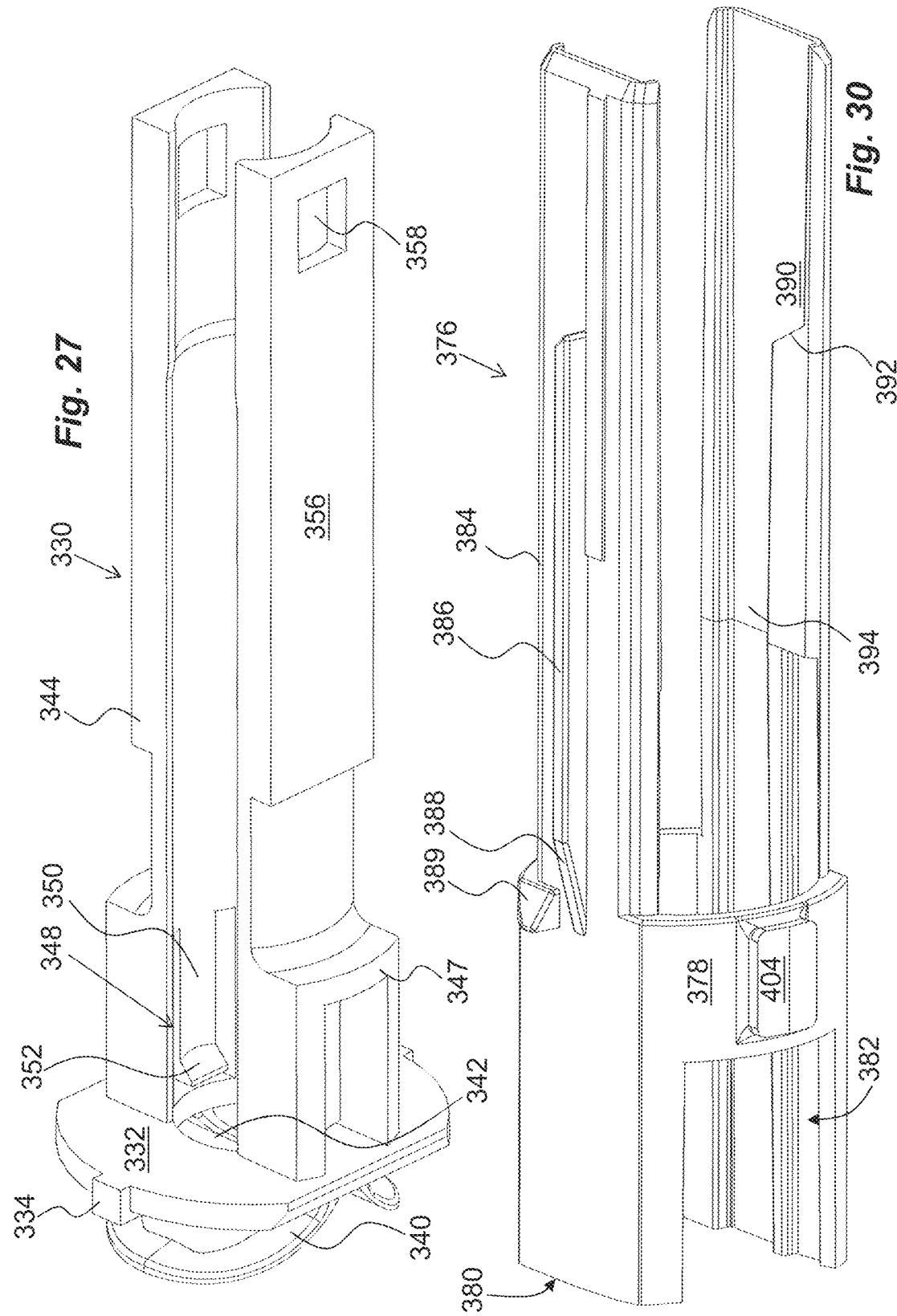

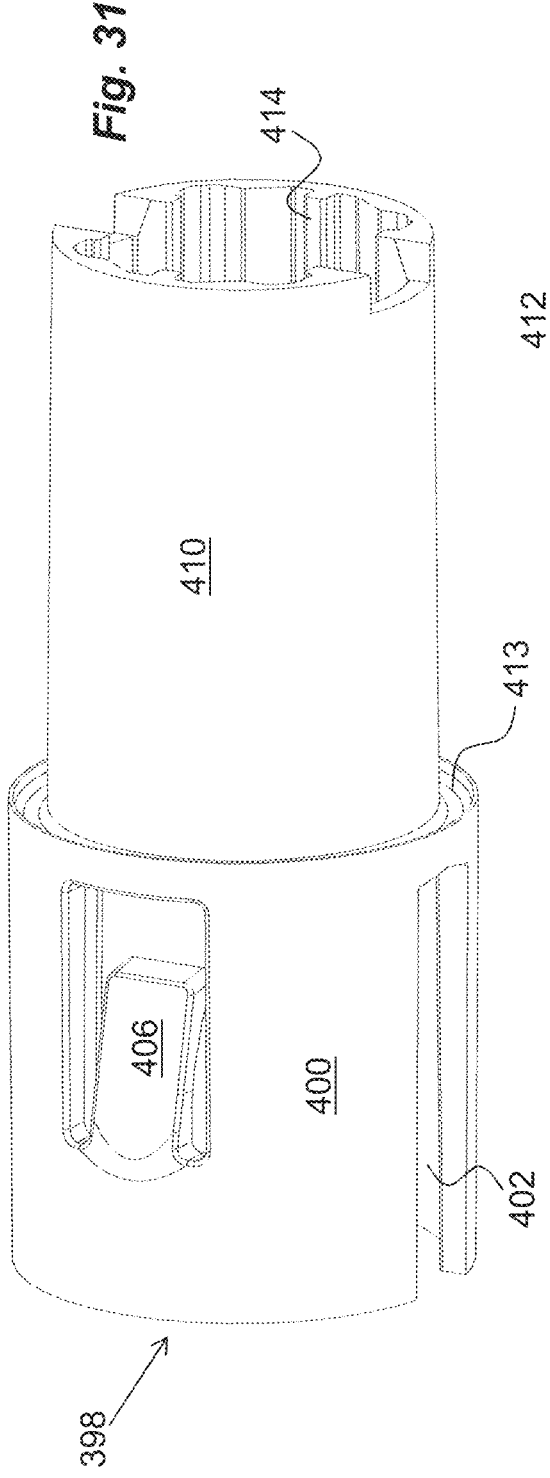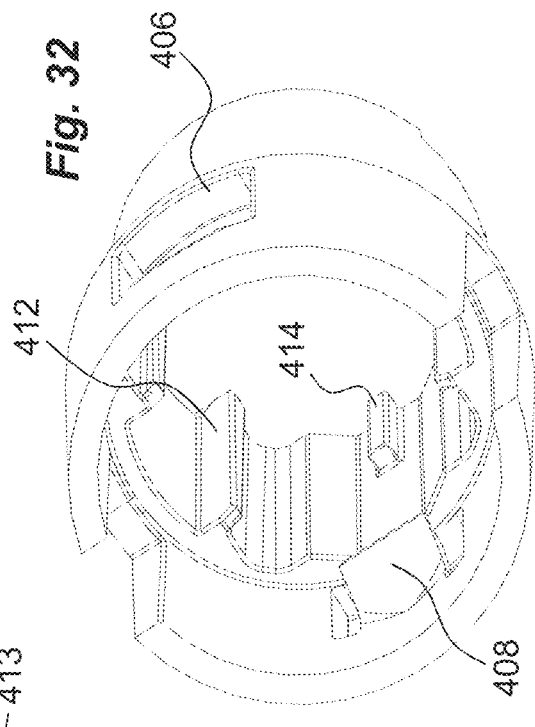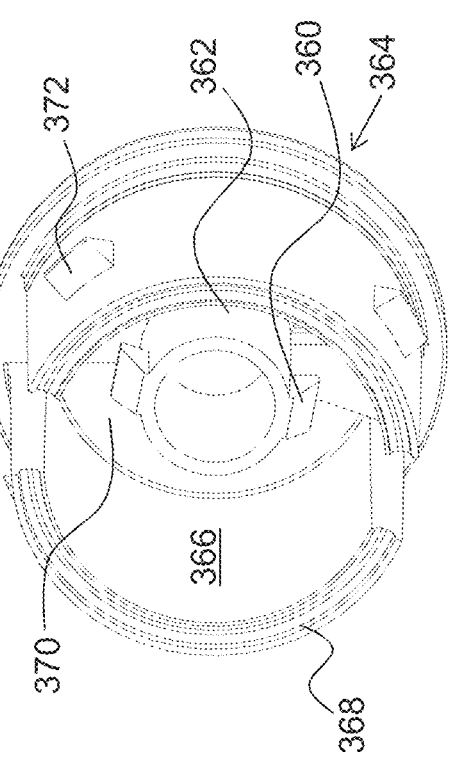

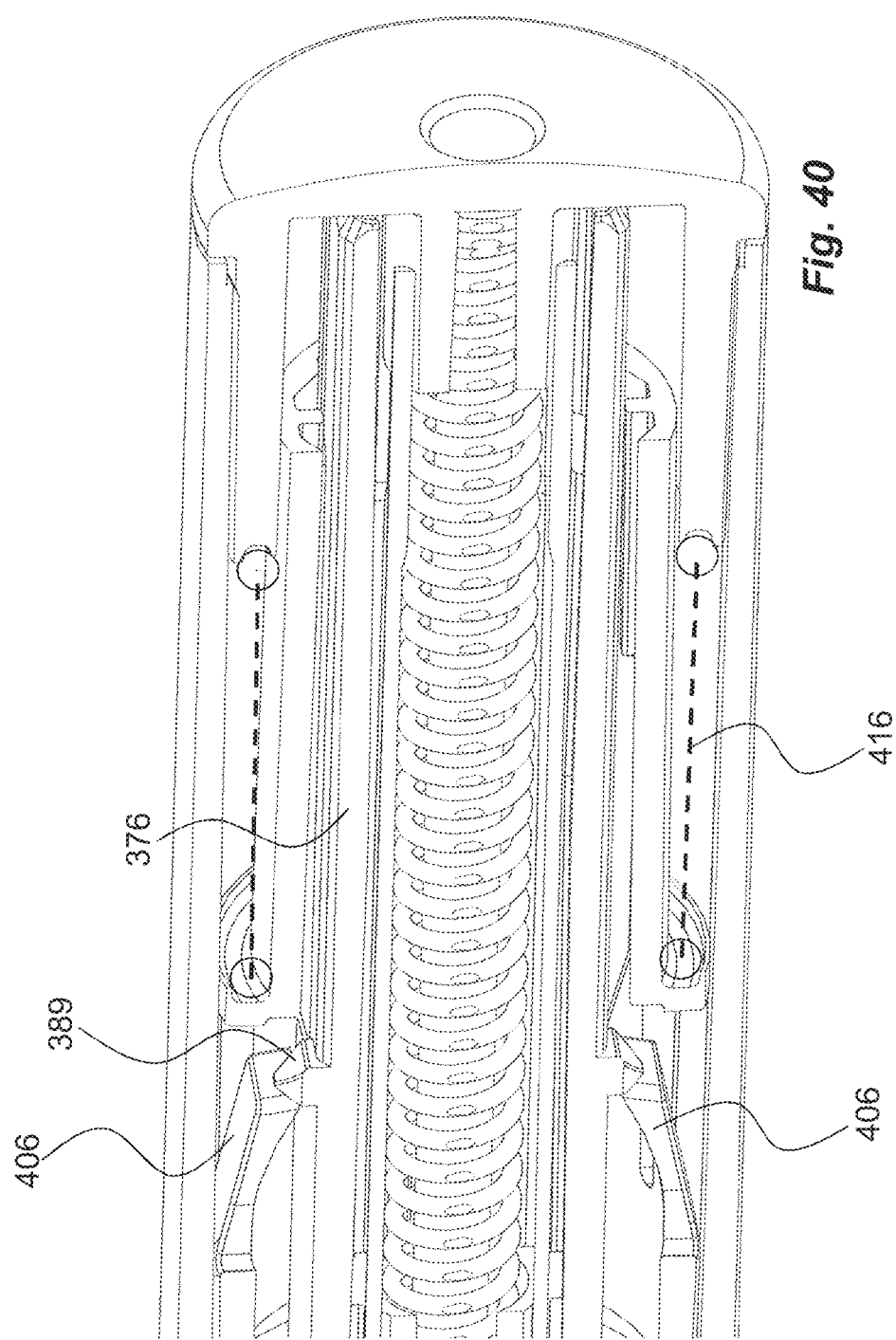

DRIVE UNIT FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2018/07423 filed Sep. 10, 2018 which claims priority to European Patent Application No. 17193709.7 filed Sep. 28, 2017. The entire disclosure contents of these applications are herewith incorporated by reference into the present application.

TECHNICAL AREA

The present disclosure pertains to medicament delivery device and in particular a medicament delivery device provided with a number of automatic functions for ease of use.

BACKGROUND

Many auto-injector solutions comprise a number of components that move generally linear inside an elongated housing for activating and/or performing different functions of the medicament delivery device, such as penetration, injection, withdrawal, medicament delivery member guard extension. The linear movement of components often entails one function per movement, which increases the complexity when several functions are to be included in the medicament delivery device.

Document WO 2011/123024 discloses a medicament delivery device provided with a number of functions that are actuated automatically in sequence when the medicament delivery device is used. In order to provide the different functions with as few components as possible, a tubular operation member or rotator is provided that is arranged with elements on its outer and inner surfaces, which elements cooperate with a number of functional elements in order to provide several functions by rotation of the rotator. This solution provides full functionality with quite few components in comparison with previous medicament delivery devices. Even though a very successful and much appreciated design, there are some aspects, of the design such as e.g. assembly that could be developed further.

SUMMARY

The aim of the present solution is to provide a medicament delivery device having several automatic functions with few components, giving a less complex and less costly medicament delivery device in comparison with state of the art medicament delivery devices.

This aim is obtained by a medicament delivery device with the features of the independent patent claim. Preferable embodiments of the medicament delivery device are the subject of the dependent claims.

According to a main aspect, a drive unit for a medicament delivery device is provided, which drive unit comprises an elongated plunger rod extending in a longitudinal direction, a drive force element capable of applying a drive force on said elongated plunger rod. Further, an actuator may be operably connected to the elongated plunger rod for releasably holding the elongated plunger rod in an energized state when the drive force element is exerting a drive force on the elongated plunger rod.

Moreover, an activator may be operably connected to the actuator for releasably holding the actuator in a holding position, wherein the actuator may be designed to be movable from the holding position in a direction generally transversal to the longitudinal direction upon a displacement of the activator for releasing the plunger rod. Thus, as opposed to conventional solutions regarding drive units for medicament delivery devices, the actuator is movable transversally instead of longitudinally for releasing the plunger rod. This may be an advantage in that the medicament delivery device containing the drive unit does not have to be made longer in order to accommodate the movement in the longitudinal direction of the actuator.

According to a further aspect, the plunger rod may be arranged with a co-acting element, in turn arranged to interact with a corresponding co-acting element on the actuator wherein the actuator may be movable in a direction generally transversal to the longitudinal direction between a holding position in which the co-acting element and the corresponding co-acting element interact with each other for releasably holding the elongated plunger rod in the energized state and a release position in which the co-acting element and the corresponding co-acting element no longer interact with each other such that the elongated plunger rod is released from the energized state. In this regard, the co-acting element may be at least one radially extending protrusion and the corresponding co-acting element may be at least one stop ledge.

According to a preferred solution, the stop ledge may have an inclination in relation to said longitudinal direction such that the force from the energized drive force element acting on the elongated plunger rod allows the radial extending protrusion to slide along the stop ledge whereby the actuator is forced to move from the holding position to the release position upon a longitudinal movement of the activator.

Further, the actuator may be arranged with a guide element interacting with the protrusion on said plunger rod. Also, the actuator may be held in the holding position by said activator, and the activator may be arranged slidable in the longitudinal direction in relation to the actuator between a first position blocking the actuator and a second position unblocking the actuator. In this regard, the activator may be arranged with guide surfaces configured to cooperate with guide surfaces of the actuator until the second position is reached by the activator. As an alternative, the activator may be rotatable between the holding position and the second position, like a generally tubular rotator.

The drive unit may further be arranged with a plunger rod holder designed to guide and support the plunger rod. The plunger rod holder may in this regard be arranged with longitudinally extending slits into which the protrusions of the plunger rod may fit and may slide. Further the plunger rod holder may be arranged with a support surface on which the actuator may rest. Also, the proximal end of the plunger rod holder, or the support surface, may be provided with resilient support elements that may interact with a distal end of a medicament container for providing movement support.

According to another favourable solution, the drive unit may be arranged with signalling elements that may interact with the plunger rod for providing audible and tactile information during the movement of the plunger rod. In this regard, the signalling elements may be arranged as resilient arms or tongues in contact with an outer surface of the plunger rod, wherein the plunger rod is arranged with protrusions and recesses that will provide sudden changes of movement of the signalling elements, thus providing the audible and tactile information.

In a favourable solution, the drive unit may comprise an end cap fixedly connected to the plunger rod holder. Further the end cap may be arranged with attachment elements for attaching the drive unit to a housing of a medicament delivery device. In this regard an activator spring may be arranged between the end cap and the activator, wherein the activator spring urges the activator in the first position.

According to a favourable solution, a medicament delivery device may comprise a drive unit according to the present application. In this regard, the medicament delivery device may comprise a housing and a medicament delivery member guard wherein the medicament delivery member guard may be slidable between an extended position and a retracted position in relation to the housing and operably connected to said activator such that a sliding movement of the medicament delivery member guard forces the activator to move.

According to a further aspect of the medicament delivery device provided with a drive unit according to the application, it may comprise a medicament container holder arranged to accommodate a medicament container. In that regard, the medicament container holder may comprise holding members for releasably holding said medicament container. In particular, the holding members may be arranged resilient for taking up any movement of the medicament container. Alternatively the holding members may be arranged as a part of the housing of a medicament delivery device.

These and other aspects of, and advantages with, the present disclosure will become apparent from the following detailed description of the disclosure and from the accompanying drawings.

BRIEF DESCRIPTION OF DRAWINGS

In the following detailed description, reference will be made to the accompanying drawings, of which FIGS. 3A and 3B are cross-sectional views of the medicament delivery device of FIG. 1, FIGS. 4, 5, 6, 7, 8, 9, 10, 11, 12 and 13 are detailed views of components comprised in the medicament delivery device of FIG. 1, FIGS. 14, 15, 16, 17, 18, 19, 20, 21 and 22 are partly cross-sectional views of the medicament delivery device of FIG. 1 showing different functional conditions, FIGS. 23, 24, 25, 26, 27, 28, 29, 30, 31 and 32 are detailed views of components of a second embodiment, and FIGS. 33, 34, 35, 36, 37, 38, 39 and 40 are partly cross-sectional views of the second embodiment showing different functional conditions.

DETAILED DESCRIPTION

Figure 1:
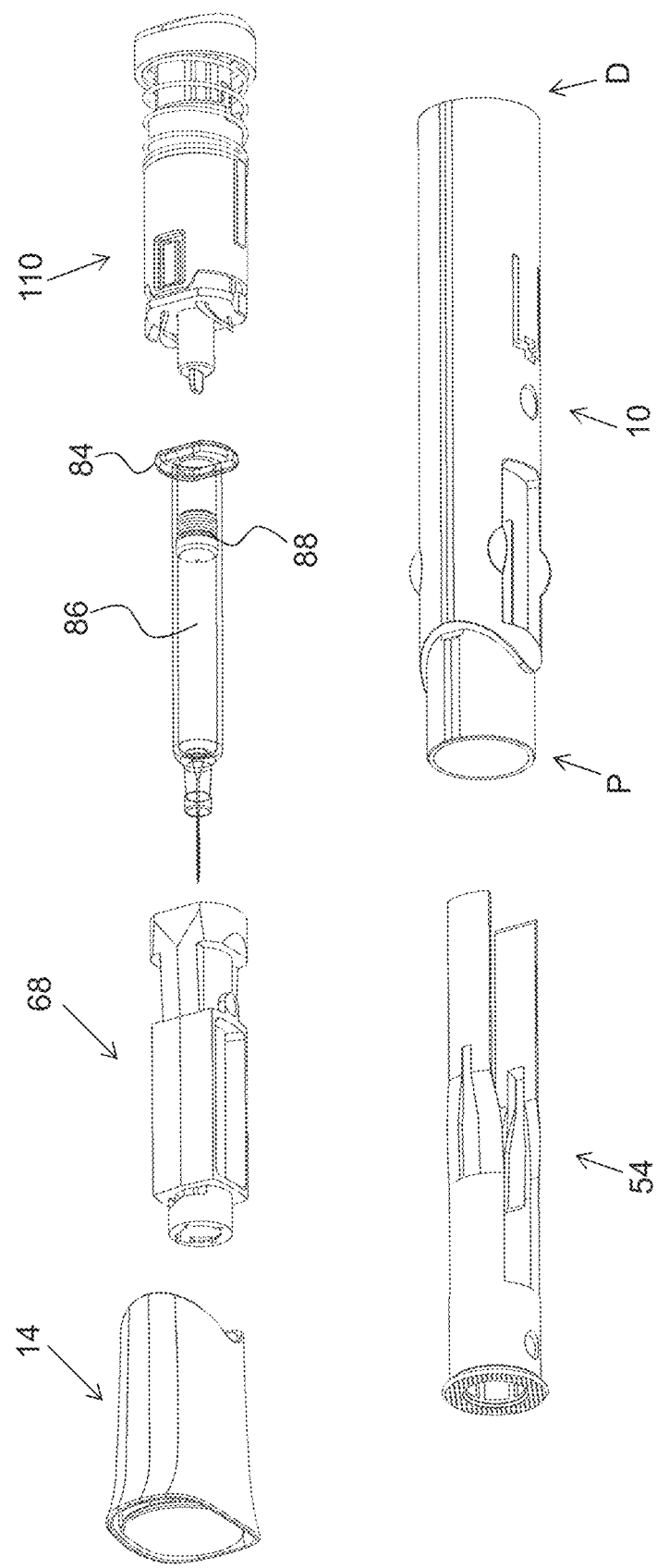
FIG. 1 is an exploded view of a first embodiment of a medicament delivery device according to the present application.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

In the present disclosure, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 2:
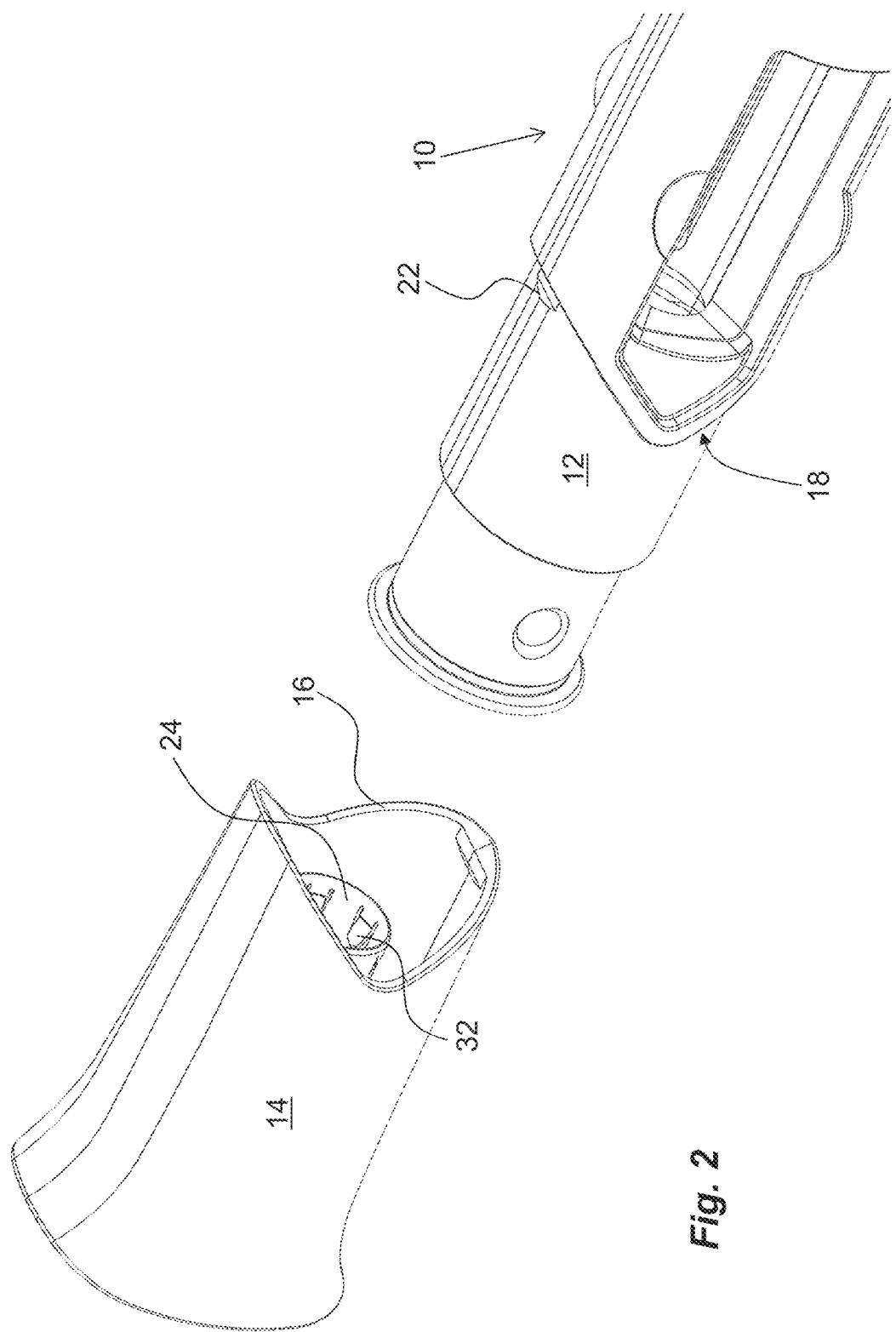
FIG. 2 is a detailed view of a proximal end of the medicament delivery device of FIG. 1 and a protective cap.

The medicament delivery device shown in the drawings comprises a generally tubular and elongated housing 10 having a proximal end P and a distal end D, FIG. 1. The proximal end of the housing is arranged with an area 12 with reduced diameter, FIG. 2, onto which area a protective cap 14 may be attached, preferably with a friction fit. A distal end surface 16 of the protective cap 14 and the proximally directed surface 18 between the reduced area 12 and the rest of the housing 10 are provided with cam-shapes so as to facilitate removal of the protective cap 14 when turning it in relation to the housing 10 such that the cam-shaped surfaces 16, 18 provide a motion in the proximal direction of the protective cap 14, FIG. 2. In addition to friction-fit connection of the protective cap 14 or instead, there may also be structural features holding the cap. In the embodiment shown, the protective cap 14 is arranged with inwardly directed protrusions 20 that are designed to interact with recesses 22 on an inner surface of the protective cap 14. The protective cap 14 is arranged with a medicament delivery member shield remover 24 that in the embodiment shown is a tubular element. It is arranged with an outwardly directed flange 26 that engages holding elements on an inner surface of a lid 30 of the protective cap 14, FIG. 3. The medicament delivery member shield remover 24 is further arranged with gripping elements 32 in the form of inwardly inclined and proximally directed tongues. The tongues 32 are intended to grip on an outer surface of a medicament delivery member shield (not shown).

The inside of the housing 10 is further arranged with a support structure at its proximal area comprising a ring-shaped, transversal, support wall 34 having a central passage 36, FIG. 4a. The support wall 34 is attached to the inner surface of the housing via two bridging parts 37 on opposite sides of the passage 36, whereby two arc-shaped passages 38 are formed between the support wall 34 and the housing 10, FIG. 4a. Distally of the arc-shaped passages 38 two longitudinally extending ledges 39 are arranged, FIG. 6, which ledges 39 have a generally dovetail shape as seen in cross-section. The bridging parts 37 are further interconnected with wall parts 40 extending inwards from the interior of the housing 10, forming a generally rectangular shape, where the material of the area in the rectangle is removed, forming a window 42, FIG. 4a. Further, a number of protrusions 44 are arranged on the outer surface of the housing 10 adjacent the windows 42, designed as stops against rolling of the medicament delivery device. It is however to be understood that the protrusions 44 may be placed on other areas of the housing 10, performing the same function.

Moreover, distally of the windows, generally U-shaped cut-outs 46 are provided, creating proximally directed tongues 48, flexible in the generally radial direction. Further a rectangular cut-out 50 is made at the free end of the tongues 48, extending into the housing, as seen in FIG. 5. On the inner surface of the housing, longitudinally extending grooves 52 are arranged from the distal end of the housing to almost the length of the tongues 48.

The medicament delivery device is further arranged with a medicament delivery member guard 54, FIGS. 6a-b, extending through a proximal passage 56 of the housing. The medicament delivery member guard 54 has a generally tubular body 58, which body 58 is arranged with a proximal circular passage 60. The proximal passage 60 is arranged with a radially extending flange 62 providing a proximally directed support surface. Further, two distally directed arms 64 are provided on a distal end of the body 58 of the medicament delivery member guard 54, wherein the arms are designed to fit into the passages 38 and extend into the housing 10. The arms 64 are designed with slits 66 that extend in the longitudinal direction. The width of the slits 66 are narrowed in the distal direction and are given a dovetail shape as seen in a cross-sectional view, the function of which will be described below. The inner surface of the body 58 is arranged with longitudinally extending ribs 67, FIG. 6b.

Coaxial with and inside the medicament delivery member guard 54 is a medicament container holder 68, FIGS. 7 and 8, having a generally rectangular body 70, which body 70 is arranged with rectangular openings 72 on opposite sides. The openings 72 are arranged with inwardly directed wall sections 74 ending in a semi-circular section of the body 70. The medicament container holder 68 is further arranged with a distal section 76 having oppositely positioned surfaces 78 that are tapering outwards in the distal direction, where the distal area 80 of the tapering surfaces 78 is arranged as a support surface. The distal end of the medicament container holder 68 is arranged with a seat 82 for a flange 84, FIG. 7, of a medicament container 86. The medicament container 86 has an elongated tubular body, in which a stopper 88 is arranged movable. The proximal end of the medicament container is provided with a medicament delivery member 90 such as an injection needle as in the embodiment shown.

Moreover, either the side surfaces of the flange 84 are completely surrounded by walls 92 of the seat 82, or by at least major wall sections. The seat 82 is further arranged with a distally directed support surface 94 for contact with the proximal surface of the flange 84. At the proximal end of the medicament container holder 68 a generally tubular support element 96 is arranged, FIG. 8, having a radially inwardly directed flange 98 at its proximal end, providing a circular passage 100 through which the medicament delivery member 90 may pass. The support element 96 is connected to the proximal end of the body 70 via an arc-shaped wall section 102. At the opposite side of the wall section 102, a slit 104 is provided through the support element 96 with its flange 98, giving the support element 96 a C-shape when viewed from the proximal end. Three more slits 106 are arranged equidistantly around the flange 98. At the ends of the "C" adjacent the slit 104, two distally directed arms 108 are arranged, FIG. 8, which arms 108 are connected to the proximal end of the body 70. The arms 108 are somewhat inclined outwards in the distal direction and are thinned out adjacent the connection points. The design of the arms 108 and the slit 104 provide a resiliently flexing action of the support element 96 as will be described.

Figure 9:
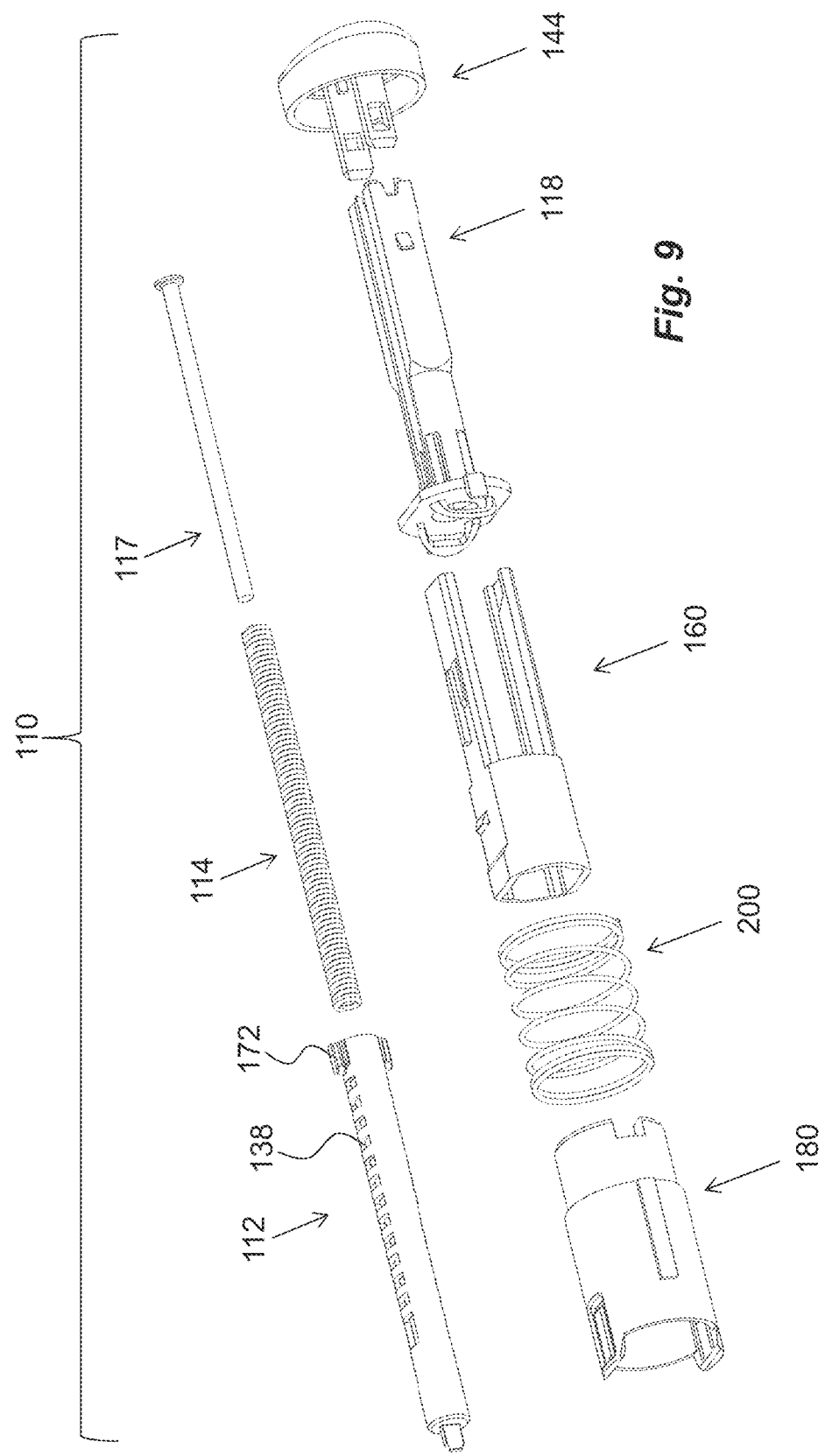

Further, the medicament delivery device comprises a power pack 110, FIG. 9. The power pack 110 comprises a generally elongated plunger rod 112. The plunger rod 112 is hollow and a drive force spring 114 is arranged inside the plunger rod 112. The drive force spring 114 is acting on a proximal end wall 116 of the plunger rod 112, FIG. 3. Inside the drive force spring a spring guide 117 is arranged. Coaxial with and outside the plunger rod 112 is a plunger rod holder 118. The plunger rod holder 118 comprises a transversal plate 120, FIG. 10, having a shape generally corresponding to the inner cross-sectional shape of the housing 10, except for two oppositely arranged cut-outs 122 such that passages are created between the plate 120 and the inner surface of the housing 10 such that the arms 64 of the medicament delivery member guard 54 can pass.

Further two outwardly directed rectangular protrusions 124 are arranged on opposite sides of the edge of the plate 120, which protrusions 124 are designed to fit into the rectangular cut-outs 50 in the housing 10, thereby locking the plunger rod holder 118 in relation to the housing 10. Further, the proximal surface of the plate 120 is arranged with proximally directed, arc-shaped, support elements 126 that are flexible in a generally longitudinal direction and are designed to be in contact with and to push the medicament container 86 in the proximal direction, thereby eliminating or minimizing any rattle or movement of the medicament container 86. A central, circular, passage 128 is arranged in the plate 120.

Further, two arms 130 are extending distally from the plate 120 of the plunger rod holder 118 on each side of the passage 128. The inwardly directed surfaces of the arms 130 have a curved shape as seen in cross-section for guiding and supporting the plunger rod 112. The plunger rod holder 118 is further arranged with signalling elements 132, FIG. 10b. The signalling elements comprise arms 134 that are arranged in the proximal direction and that are flexible in the generally radial direction. The free ends of the arms 134 are interconnected with contact elements 136 such as transversal beams. The transversal beams 136 are designed to be in contact with the plunger rod 112 and in particular a plurality of protrusions and/or recesses 138 along the plunger rod 112 for creating sounds and perhaps vibrations when the plunger rod 112 is moved in relation to the plunger rod holder 118 as will be described.

The distal ends of the arms 130 are arranged with outwardly planar surfaces 139 and on these surfaces, wedge-shaped protrusions 140 are provided. The wedge-shaped protrusions 140 are to interact with recesses 141 in proximally directed arms 142 of an end cap 144, FIG. 11. The arms 142 are attached to a generally dome-shaped body 146 of the end cap 144. A proximal surface of the body 146 is arranged with a seat 148 in which a distal end of the spring guide 117 as well as the distal end of the drive spring 114 are placed. Further, longitudinally directed ribs 152 are arranged on the inner surfaces of the arms 142. The ribs 152 are designed to interact with cut-outs 154 in the distal ends of the arms 130 of the plunger rod holder 118.

The power pack 110 further comprises an actuator 160 that hereafter will be called slider 160, FIG. 12. The slider 160 comprises a hollow tubular body 162 arranged coaxial with and surrounding the plunger rod holder 118. The tubular body has a proximally directed end surface 163 that is arranged to be in contact with a distally directed surface of the plate 120 of the plunger rod holder 118. The interior of the body 162 of the slider 160 is arranged so that it may move transversally in relation to the arms 130 of the plunger rod holder 118 as will be described. The body 162 of the slider 160 is arranged with two distally directed arms 164 that are generally planar on both the outside and the inside. The inner surfaces of the slider 160 are arranged with longitudinally extending grooves 166. At the distal end of the arms 164, the grooves 166 are connected to cut-outs 168, which cut-outs 168 are arranged with inclined, distally directed support surfaces 170. The cut-outs 168 and the grooves 166 are to interact with radially directed protrusions 172 on a distal end of the plunger rod 112, as will be described. On the outer surfaces of the arms 164 longitudinal ledges 174 are arranged, forming guide surfaces. The ledges 174 are bevelled at the distal ends. Further on one side of the ledges 174, elevated areas 176 are arranged, the function of which will be described. Further transversally arranged wedge-shaped protrusions 178 are arranged on the outer surfaces of the arms 164.

An activator, hereafter named lock sleeve 180, FIG. 13, with a generally tubular body 182 is arranged coaxial with and slidable inside the housing 10 from the distal end thereof. The outer surface of the body 182 of the lock sleeve 180 is arranged with longitudinally extending ledges 184, which ledges 184 are arranged to fit into the longitudinal grooves 52 on the inner surface of the housing 10, preventing rotation of the lock sleeve 180. The lock sleeve 180 is further arranged with proximally directed tongues 188 that are flexible in the generally radial direction. The free ends of the tongues 188 are arranged with inwardly directed protrusions 190. Further a distal end of the lock sleeve 180 is provided with two longitudinally extending ledges 192 positioned opposite each other, forming guide surfaces. The ledges 192 are to interact with the outwardly ledges 174 of the slider 160 as will be described. Further a number of inwardly directed ledges 194 are provided, forming guide surfaces for the slider 160 and for the plunger rod holder 118. Moreover, the distal area 196 of the lock sleeve 180 has a smaller diameter than the rest of the body 182, creating a distally directed annular ledge 198. A lock sleeve spring 200 is arranged between the distal ledge 198 of the lock sleeve 180 and the proximal surface of the end cap 144.

The medicament delivery device is intended to be assembled as follows. A medicament container 86 such as a syringe is provided with a medicament delivery member shield such as a rigid needle shield or RNS. The medicament container 86 with the RNS is inserted into the medicament container holder 68 from the distal end. When the RNS enters the passage 100 of and comes in contact with the C-shaped support element 96 of the medicament container holder 68, the RNS will cause the support element 96 to flex in the radial direction against the force of the inclined arms 108 due to the slit 104. When the inwardly directed flange 98 of the support element has passed the RNS, the support element 96 can flex back to its original position, being in contact with a shoulder portion of the medicament container 86.

The medicament delivery member guard 54 is inserted from the front into the housing of the medicament delivery device wherein the arms 64 of the medicament delivery member guard 54 will pass the arc-shaped passages 38 and will flex inwardly when in contact with the dovetail ledges 39 until the ledges 39 are placed in the wider area of the slits 66 of the medicament delivery member guard 54, permitting the arms 64 to flex outwards so that the ledges 39 are placed in the slits 66. The medicament delivery member guard 54 is then pulled in the proximal direction whereby the dovetail ledges 39 enter into the dovetail part of the slits 66. The medicament container holder 68 is then inserted into the medicament delivery member guard 54.

Figure 15:
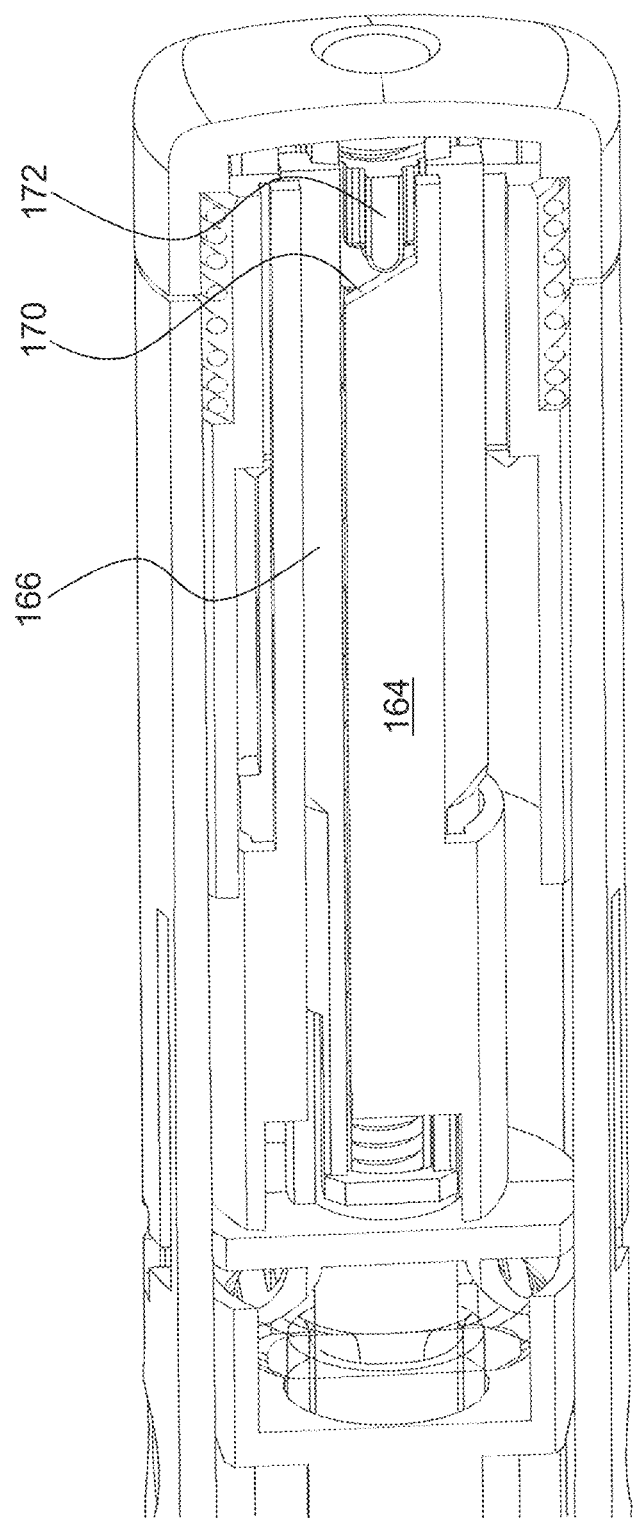

The power pack 110 is assembled in that the slider 160 is pushed onto the plunger rod holder 118 from the distal end thereof until the proximal end surface 163 is in contact with the distal surface of the plate 120. The lock sleeve 180 is then pushed onto the slider 160 wherein the inner ledges 192 of the lock sleeve 180 are positioned to the right of the outer ledges 174 on the slider 160 when the medicament delivery device is held vertically with the proximal end facing down, as seen in FIG. 14. The slider 160 is then in an initial position transversally. The plunger rod 112 is then inserted into the plunger rod holder 118 and in this position of the slider 160 the protrusions 172 of the plunger rod 112 are in contact with the inclined support surfaces 170 of the cut-outs 168 on the inner surfaces of the slider 160, FIG. 15, and the plunger rod 112 is thus prevented from moving in the proximal direction in relation to the slider 160. The drive force spring 114 is now entered into the plunger rod 112 together with the spring guide 150.

After this, the distal ends of the drive force spring 114 and the spring guide 150 are placed in the seat 148 of the end cap 144 and the end cap 144 is pushed in the proximal direction towards the plunger rod holder 118, thereby tensioning the drive force spring 114. The end cap 144 is connected and locked to the plunger rod holder 118 when the wedge-shaped protrusions 140 on the plunger rod holder 118 enter into the recesses 141 of the arms 142 of the end cap 144. Apart from the tensioning of the drive force spring 114, the lock sleeve spring 200 arranged between the end cap 144 and the lock sleeve 180 is also tensioned when the end cap 144 is pushed onto the plunger rod holder 118.

When now a power pack 110 is to be assembled with an assembled housing 10 the proximal end of the power pack 110 is entered into the distal end of the housing 10 and is pushed until the rectangular protrusions 124 on the plate 120 of the plunger rod holder 118 pass the tongues 48 of the housing 10 and fit into the rectangular cut-outs 50 in the tongues 48 and in the housing 10. At the same time the arc-shaped support elements 126 of the plunger rod holder 118 are moved in contact with a distal surface of the flange 84 of the medicament container 86, pushing it in the proximal direction for eliminating rattle. Further the protective cap 14 is connected to the proximal end of the medicament delivery device. The medicament delivery member shield remover 24 is then pushed over the medicament delivery member shield and is guided by the ribs 67 on the inner surface of the body 58 of the medicament delivery member guard 54. These ribs 67 also act as support surfaces for the medicament delivery member shield should the medicament delivery device be dropped such that the protective cap 14 hits a surface at an angle. This impact causes a bending force on the medicament delivery member shield from the medicament delivery member shield remover 24, which may cause a breakage of the proximal part of the medicament container 86. This bending force is now taken up by the ribs 67.

Figure 16:
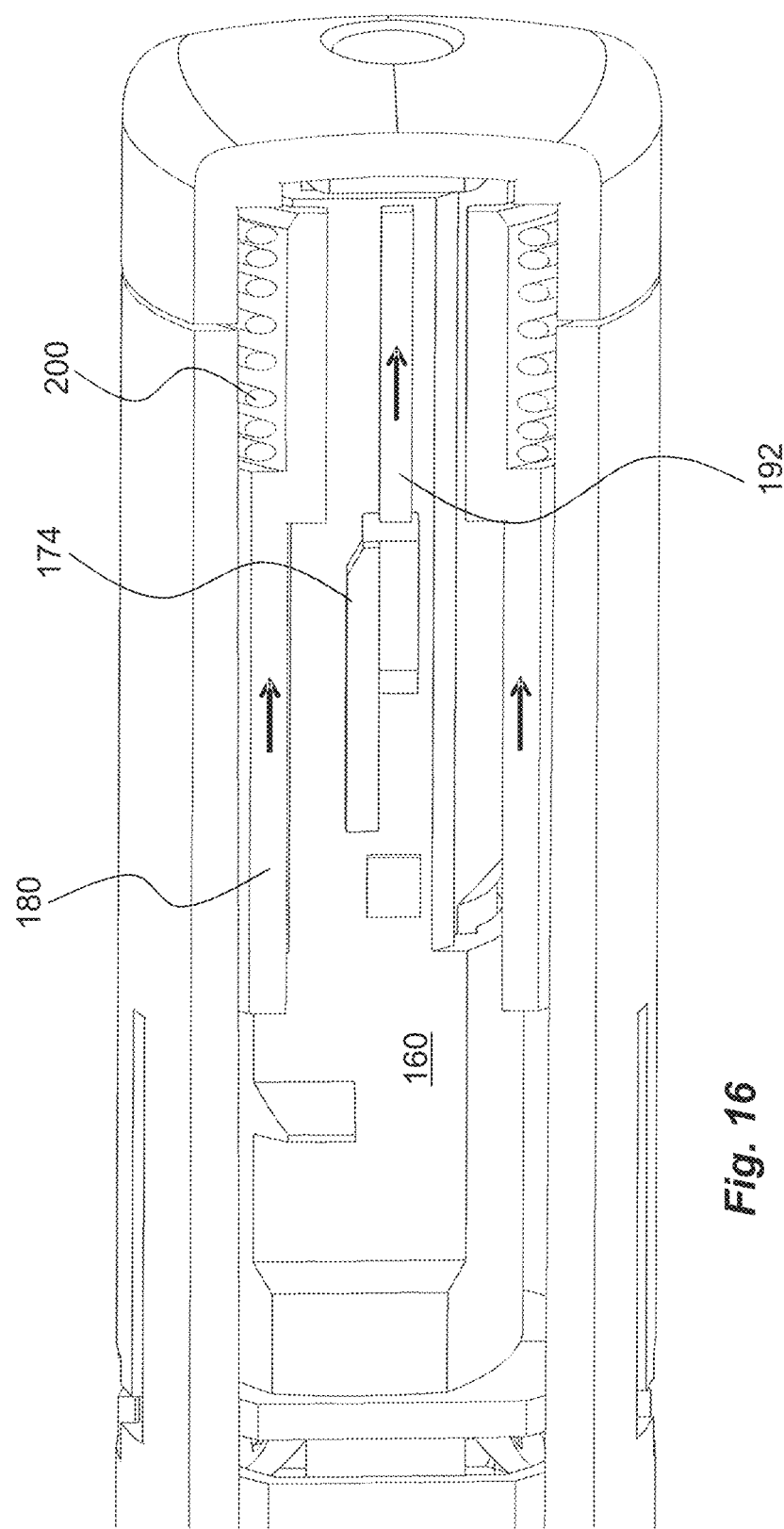

The medicament delivery device is now ready to be used. The user then removes the protective cap 14, either by pulling and/or by twisting the protective cap in relation to the housing. This movement causes the gripping elements 32 to engage with the material of the medicament delivery member guard such that the medicament delivery member guard is removed from the medicament delivery member 90. The next step is to place the proximal end of the medicament delivery member guard 54 at a dose delivery site and press the medicament delivery device towards the site. The medicament delivery member guard 54 will then move distally in relation to the rest of the medicament delivery device. Because the distal end surfaces of the medicament delivery member guard 54 are in contact with the lock sleeve 180, the latter will also move distally, compressing the lock sleeve spring 200. The inner ledges 192 of the lock sleeve 180 will slide along the outer ledges 174 of the slider 160 until the distal edge of the lock sleeve ledge 192 is moved out of contact with outer ledge 174 of the slider 160, thereby releasing the slider 160, FIG. 16.

Figure 17:
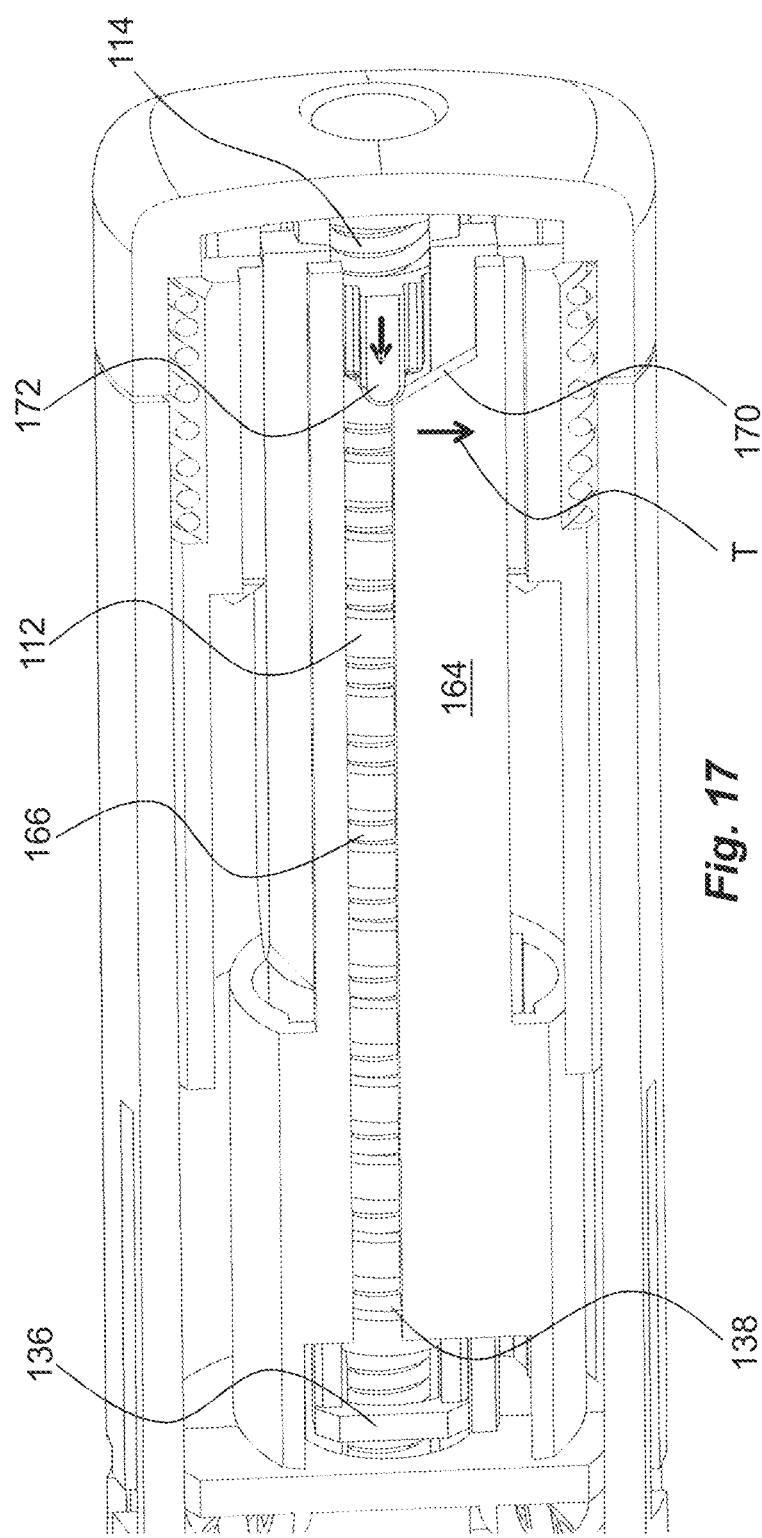
Figure 18:
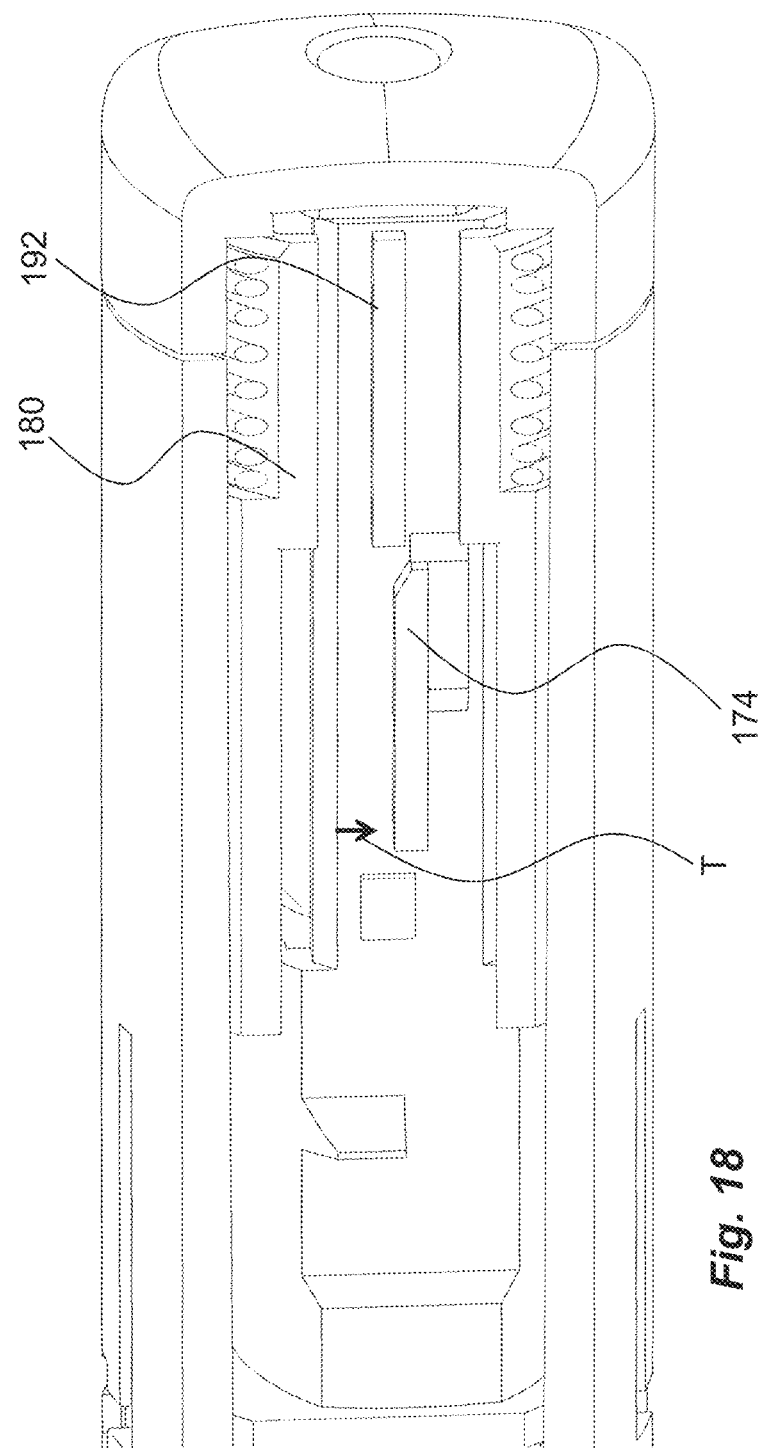

When now the slider 160 is released, its distal area is moved generally transversally, as indicated by arrow T, by the force from the protrusions 172 of the tensioned plunger rod 112 on the inclined support surfaces 170 of the cut-outs 168 such that the protrusions 172 of the plunger rod 112 will move to the longitudinal grooves 166 on the inside of the slider 160, FIG. 17. However, due to the point of contact between the inclined support surfaces 170 and the protrusions at the distal area of the slider 160, there will be a tilting movement of the slider 160. In order to facilitate this, the proximal end surface 163 of the slider 160 being in contact with the distal surface of the plate 120 of the plunger rod sleeve 118 may be somewhat rounded in order to reduce the forces for moving the slider 160, FIG. 13c. The transversal movement of the distal area of the slider has also moved its ledge 174 transversally in relation to the ledge 192 of the lock sleeve 180 as seen in FIG. 18.

Figure 19:
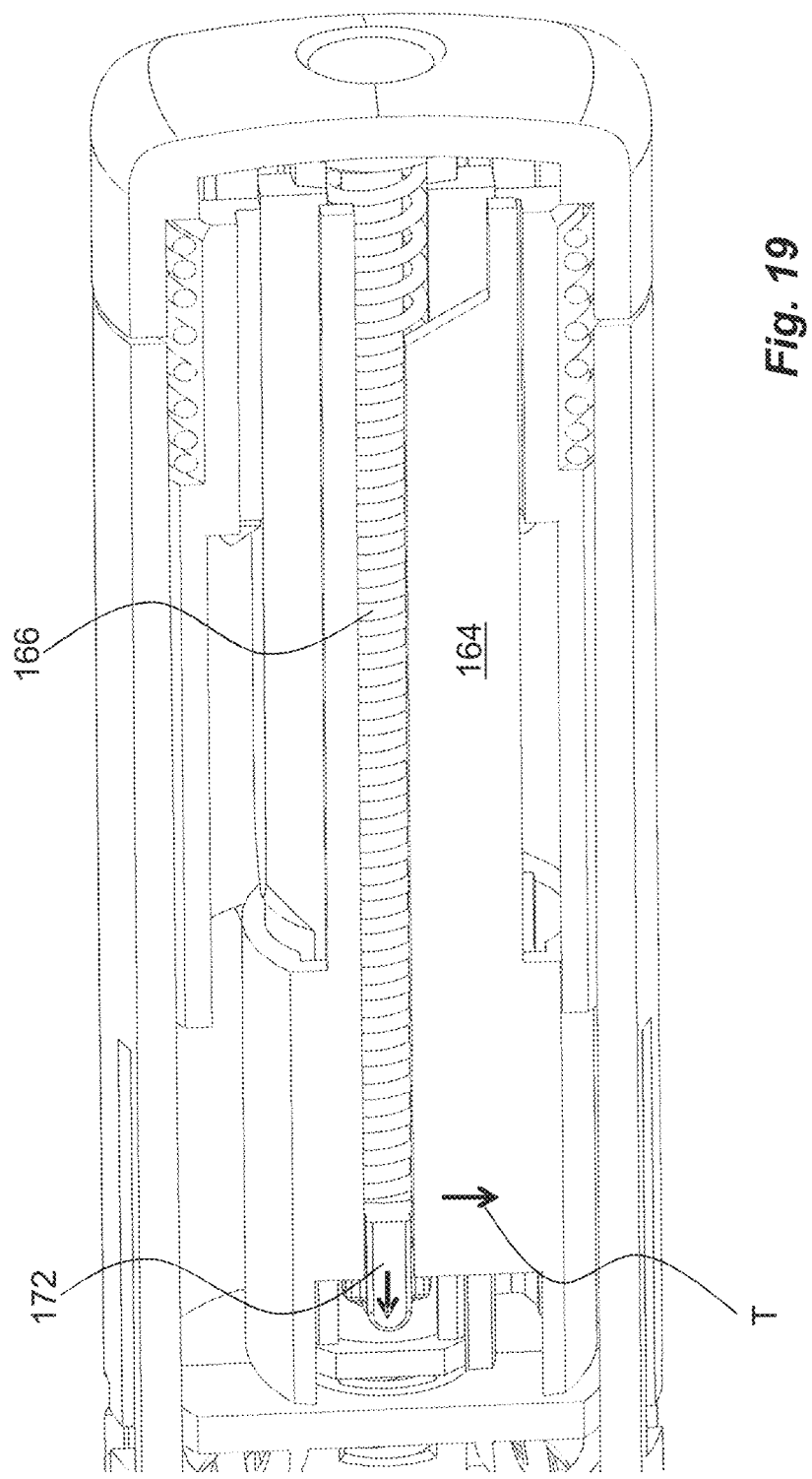
Figure 20:
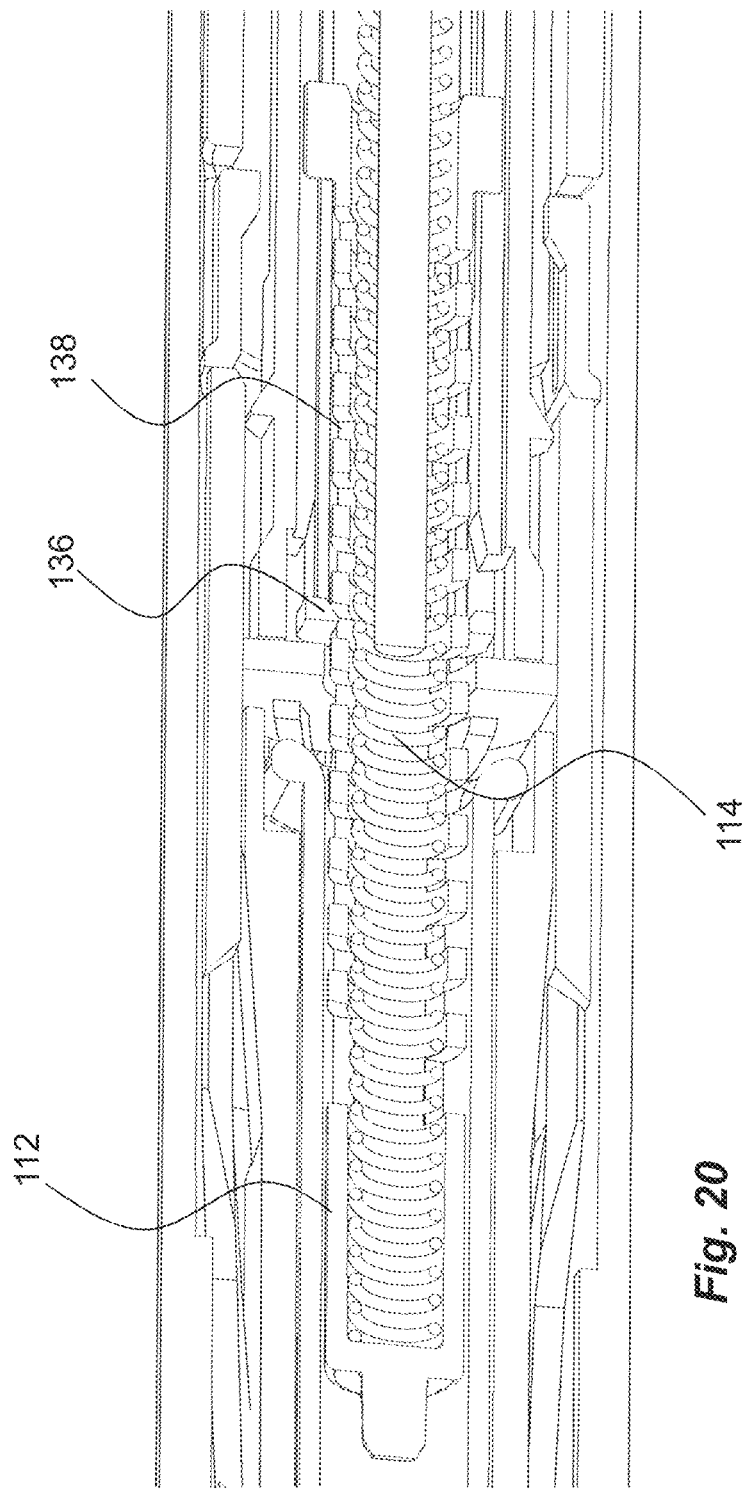

The plunger rod 112 is now free to move in the proximal direction by the drive spring 114, whereby the protrusions 172 of the plunger rod 112 slide along the grooves 166 pushing also the rest of the slider 160 in the generally transversal direction, FIG. 19. The movement of the plunger rod 114 causes the stopper 88 of the medicament container 86 to be moved, in turn causing a dose of medicament to be delivered to the dose delivery site through medicament delivery member 90. During the dose delivery sequence, the signalling elements 132 are active and indicate to a user that the sequence is ongoing in that the beams 136 move over the protrusions/recesses 138 of the plunger rod 112, FIG. 20. When the signalling elements 132 become inactive at the end of the dose delivery sequence, this indicates to the user that it is safe to remove the medicament delivery device from the dose delivery site.

Figure 21:
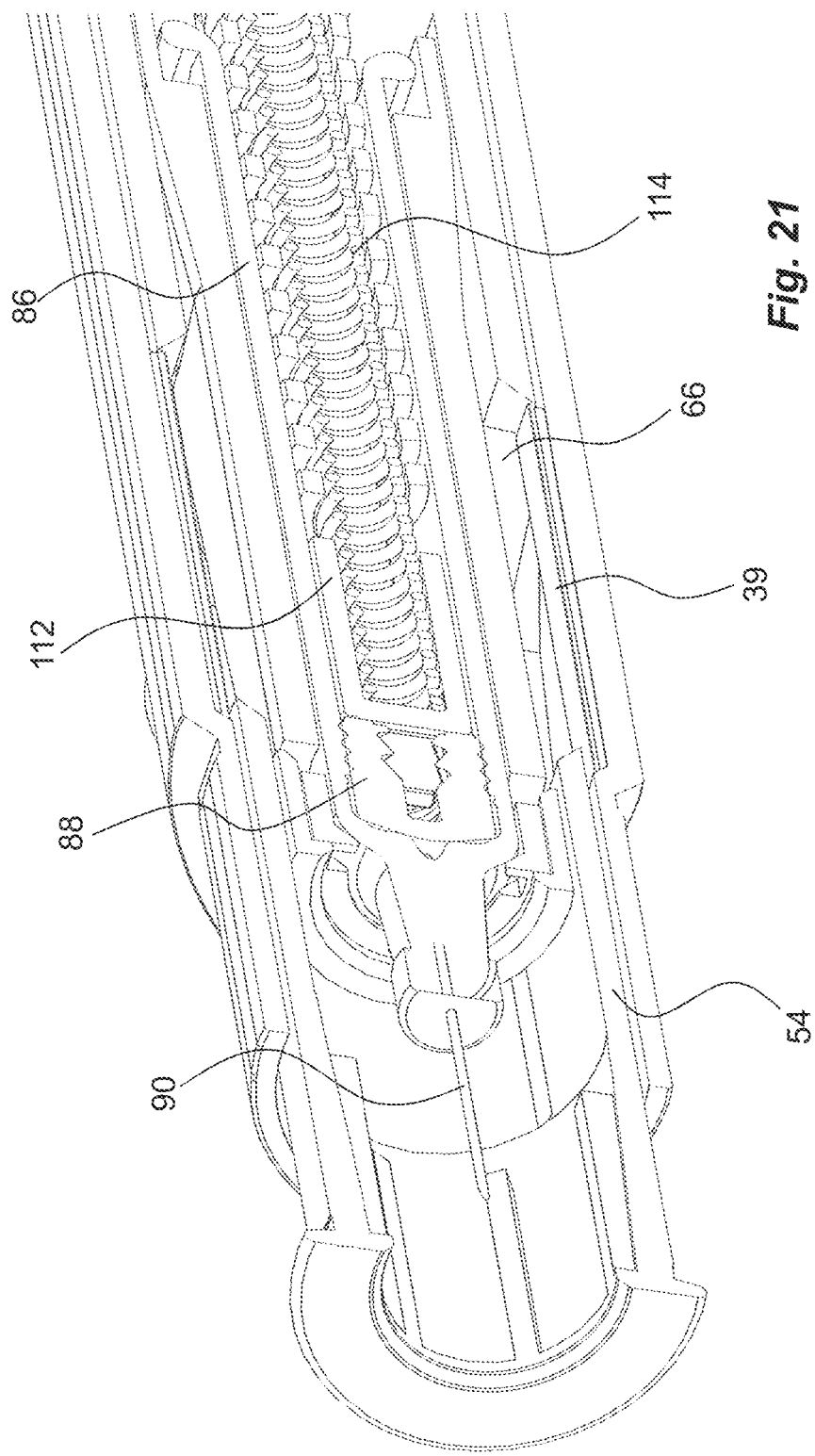
Figure 22:
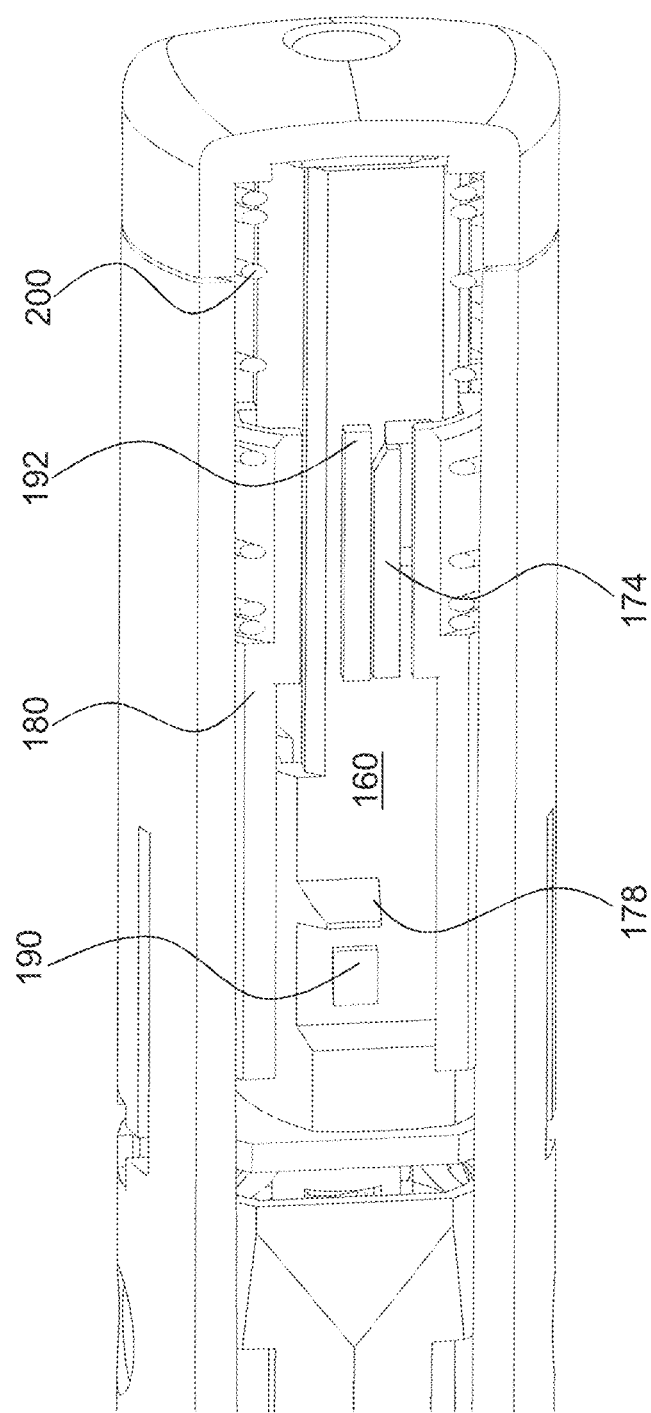

When now the medicament delivery device is removed, the medicament delivery member guard 54 is free to be pushed in the proximal direction by the lock sleeve spring 200 acting on the lock sleeve 180 until the dovetail ledges 39 on the inner surface of the housing 10 come in contact with the distal ends of the slits 66 in the medicament delivery member guard 54, FIG. 21, whereby the medicament delivery member 90 is covered by the medicament delivery member guard. The movement of the lock sleeve 180 further causes its ledges 192 to pass the ledges 174 of the slider 160 on the opposite side as seen in FIG. 22. Moreover, the movement of the lock sleeve 180 in the proximal direction will cause the protrusions 190 on the flexible tongues 188 of the lock sleeve 180 to come in contact with, and move over, the wedge-shaped protrusions 178 of the slider 160 that are now aligned in the in longitudinal position, FIG. 22, thereby locking the lock sleeve 180 and thus the medicament delivery member guard 54 in the distal direction. The device is now safe to discard.

Figure 23:
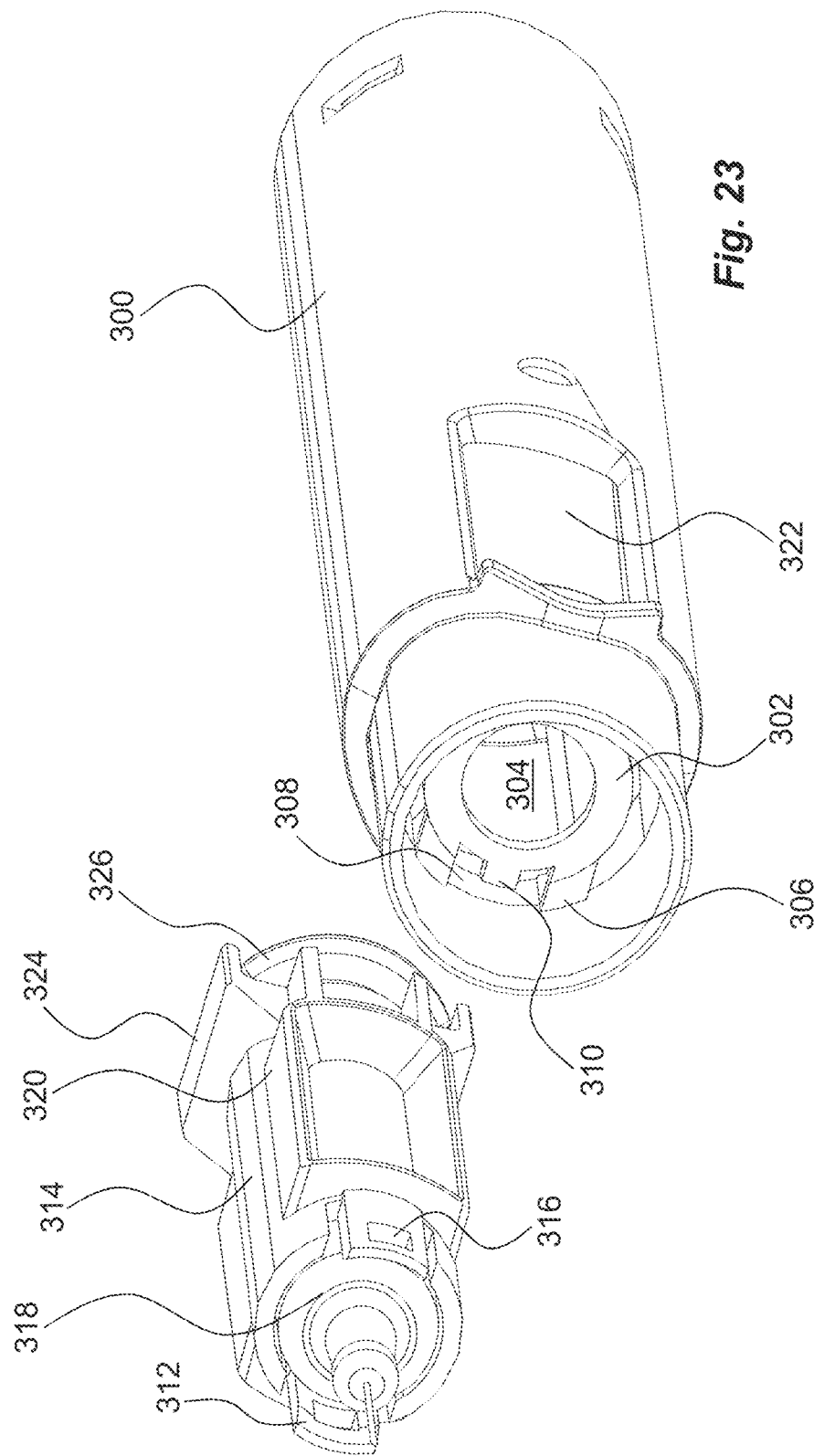

FIGS. 23-40 display a second embodiment of the medicament delivery device according to the present application. A housing 300 of the second embodiment has a transversal wall 302 having a central passage 304, FIG. 23. Bridging parts 306 are connecting the transversal wall 302 with the inner surface of the housing 300. The bridging parts 306 are arranged with passages 308, which passages 308 are provided with radially outwardly directed protrusions 310. These protrusions 310 are intended to interact with proximally directed tongues 312 of a medicament container holder 314 that will fit into the passages 308. The tongues 312 of the medicament container holder 314 are further arranged with cut-outs 316 in which the protrusions 310 fit, for locking the medicament container holder 314 to the housing both rotationally and axially, FIG. 24. The medicament container holder 314 of this embodiment does not have a support element at the proximal end. Instead, the transversal wall 302 of the housing 300 acts as a support element for the proximal end of a medicament container 318, wherein the neck portion of the medicament container 318 rests against the distally directed circumferential surface of the transversal wall 302 around the central passage 304. The side surfaces of the medicament container holder 314 are further arranged with rectangular wall sections 320 that will be aligned with openings 322 of the housing 300 as seen in FIG. 24. The distal end of the medicament container holder 314 is provided with support surfaces 324 for a flange 326 of the medicament container 318, FIG. 23.

Figure 26:
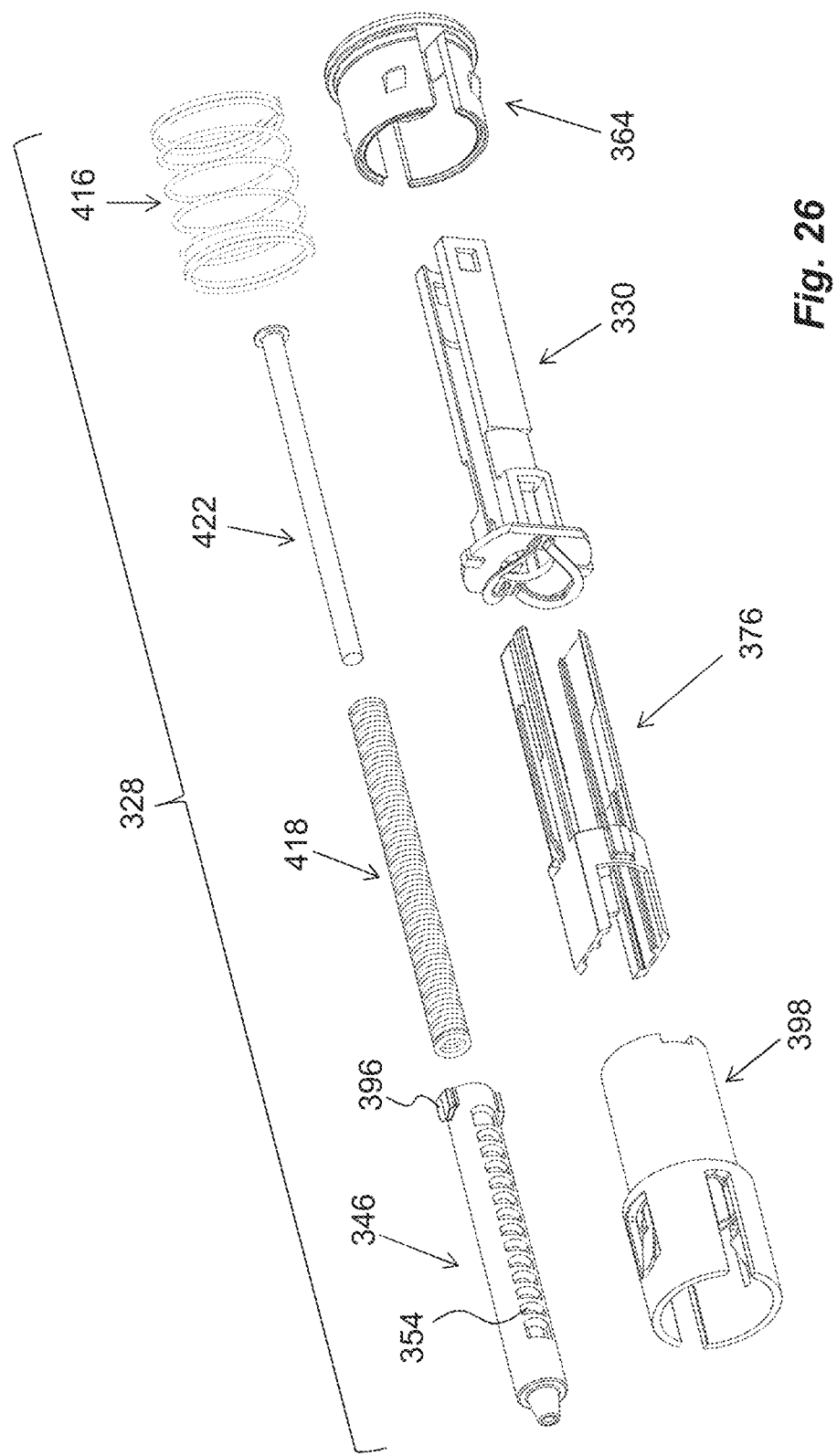

Further, the power pack 328 of the embodiment is arranged with some modified components, which will be described. As seen in FIGS. 26 and 27, a plunger rod holder 330 is provided with a proximal end plate 332. The outer surface of the end plate 332 is provided with outwardly directed protrusions 334 that fit into longitudinal grooves 336 on the inner surface of the housing 300, FIG. 28. The grooves 336 end at an abutment 338, stopping the plunger rod holder 330 in the proximal direction. Further, the proximal surface of the end plate 332 is arranged with proximally directed, arc-shaped, support elements 340 that are flexible in a generally longitudinal direction and are designed to be in contact with and to push the medicament container 318 in the proximal direction, thereby eliminating or minimizing any rattle or movement of the medicament container 318. A central, circular, passage 342 is arranged in the end plate 332.

The end plate 332 is further arranged with distally directed arms 344 with curved inner surfaces that will enclose a plunger rod 346. The parts of the arms 344 adjacent the end plate 332 are formed as outwardly directed rectangular protrusions 347. In these protrusions 347, signalling elements 348 are arranged in the form of proximally directed tongues 350 that are flexible in the general radial direction. The free ends of the tongues 350 are provided with inwardly directed ledges 352, which ledges 352 are arranged to cooperate with protrusions/recesses 354 on the outer surface of the plunger rod 346. The distal areas of the arms 344 have generally planar outer surfaces 356.

The distal ends of the arms 344 of the plunger rod holder 330 are arranged with cut-outs 358. These cut-outs 358 are to cooperate with outwardly directed ledges 360 on a central, proximally directed tubular post 362 attached to a proximally directed surface of an end cap 364, FIG. 29. The end cap 364 has a generally tubular body 366, which body 366 has a proximal end surface forming a proximally directed ledge 368. An end wall 370 is attached to or made integral with the body 366. The post 362 has a diameter generally corresponding to the cross-sectional dimensions of the arms 344 of the plunger rod holder 330 wherein the post 362 fits in between the arms 344 and the ledges 360 fit into the cut-outs 358, locking the end cap 364 to the plunger rod holder 330. Further the end cap 364 is arranged with outwardly directed protrusions 372 that are to interact with cut-outs 374 at a distal area of the housing 300, thereby locking the end cap 364 to the distal end of the housing 300.

Coaxial with and surrounding the plunger rod holder 330 is an actuator 376, hereafter named slider, FIGS. 26 and 30. The slider 376 comprises a generally tubular body 378 at its proximal end. The proximal end surface 380 of the slider 376 is designed to be in contact with a distal surface of the end plate 332 of the plunger rod holder 330. The proximal end surface 380 is preferably somewhat rounded as with the previous embodiment. The body 378 of the slider 376 is further arranged with rectangular cut-outs 382, in which the rectangular protrusions 347 of the plunger rod holder 330 fit. The body 378 of the slider 376 is arranged with two distally directed, generally planar, arms 384. The outer surfaces of the arms 384 are arranged with generally longitudinally extending ledges 386. The proximal ends of the ledges 386 are provided with bevelled surfaces 388. The outer surfaces of the arms are further arranged with outwardly directed wedge-shaped protrusions 389 forming stop ledges. The inner surfaces of the arms 384 are arranged with cut-outs 390 at their distal ends, wherein the cut-outs 390 are provided with inclined support surfaces 392. From the cut-outs 390, longitudinal grooves 394 are arranged, running all the way to the proximal end of the slider 376. The cut-outs 390 and the longitudinal grooves 394 are intended and designed to accommodate outwardly directed protrusions 396 on a distal end of the plunger rod 346.

Coaxial with and outside the slider 376 is an activator 398, hereafter named lock sleeve, FIGS. 26, 31 and 32. The lock sleeve 398 has a generally tubular first proximal body part 400. The first body part 400 is arranged with generally rectangular cut-outs 402, in which generally rectangular protrusions 404 on the outer surface of the slider 376 fit. The first body part 400 is further arranged with distally directed tongues 406, flexible in the generally radial direction. The tongues 406 are inclined somewhat inwardly and the free ends of the tongues 406 are arranged with distally directed stop surfaces 408. The lock sleeve 398 is further arranged with a generally tubular second distal body part 410. The second body part 410 has a diameter smaller than the first part, creating a distally directed ledge 412. The inner surface of the second body part 410 is provided with longitudinally extending support ledges 413, arranged to be in contact with the planar outer surfaces 356 of the plunger rod holder 330 and support it in the transversal direction. The inner surface of the second body part 410 is further arranged with longitudinally extending guide ledges 414, which guide ledges 414 are to interact with the ledges 386 of the slider 376 as will be described. A lock sleeve spring 416, FIGS. 25 and 26, is arranged between the distally directed ledge 412 of the lock sleeve 398 and the proximally directed ledge 368 of the end cap 364, biasing the lock sleeve 398 in the proximal direction. Further a drive spring 418, FIGS. 25 and 26, is arranged inside the plunger rod 346 with a proximal end in contact with a transversal proximal end wall 420 of the plunger rod 346 and a distal end in contact with the end wall 370 of the end cap 364, FIG. 25. Inside the drive spring 418 a spring guide 422 is arranged.

Figure 34:
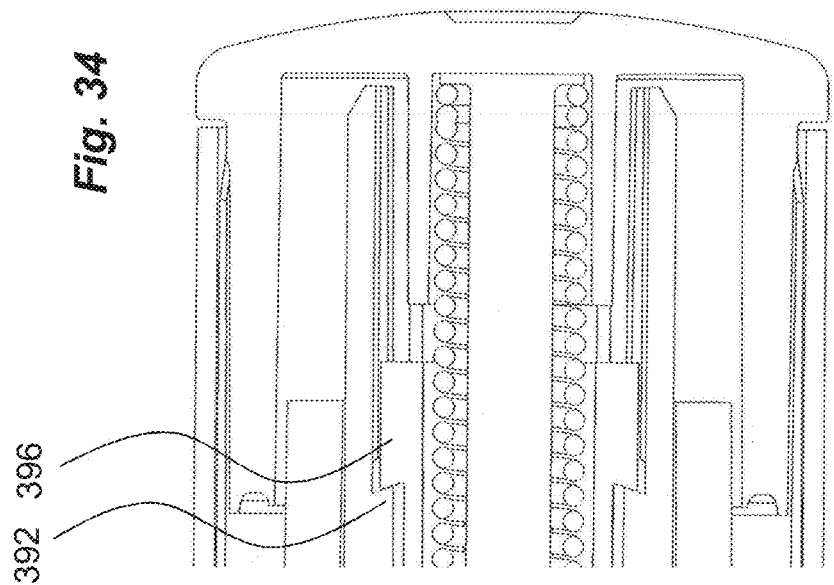
Figure 33:
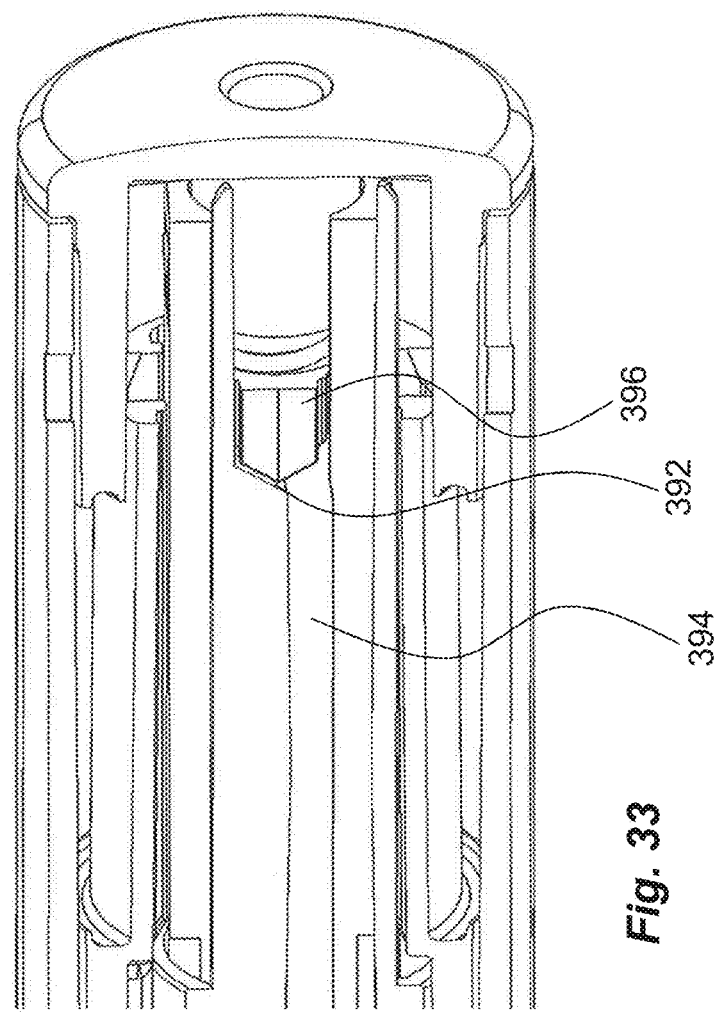
Figure 35:
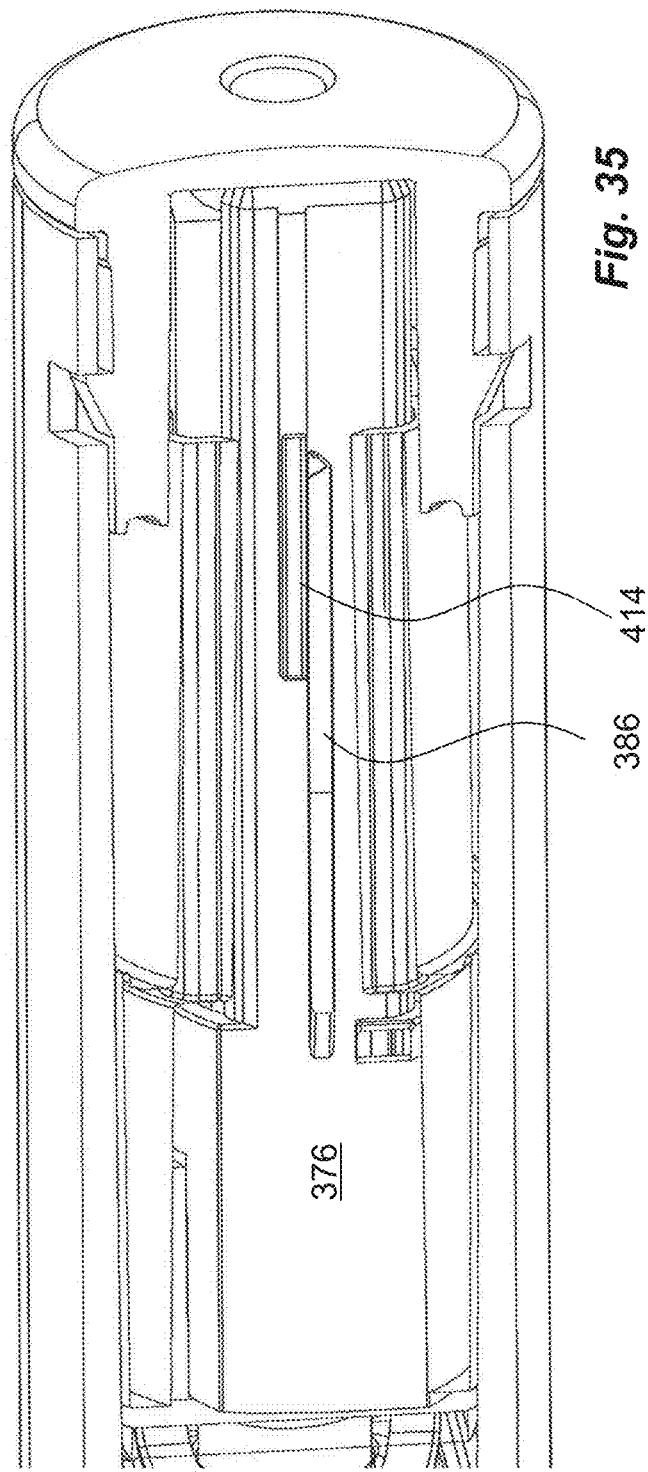
Figure 36:
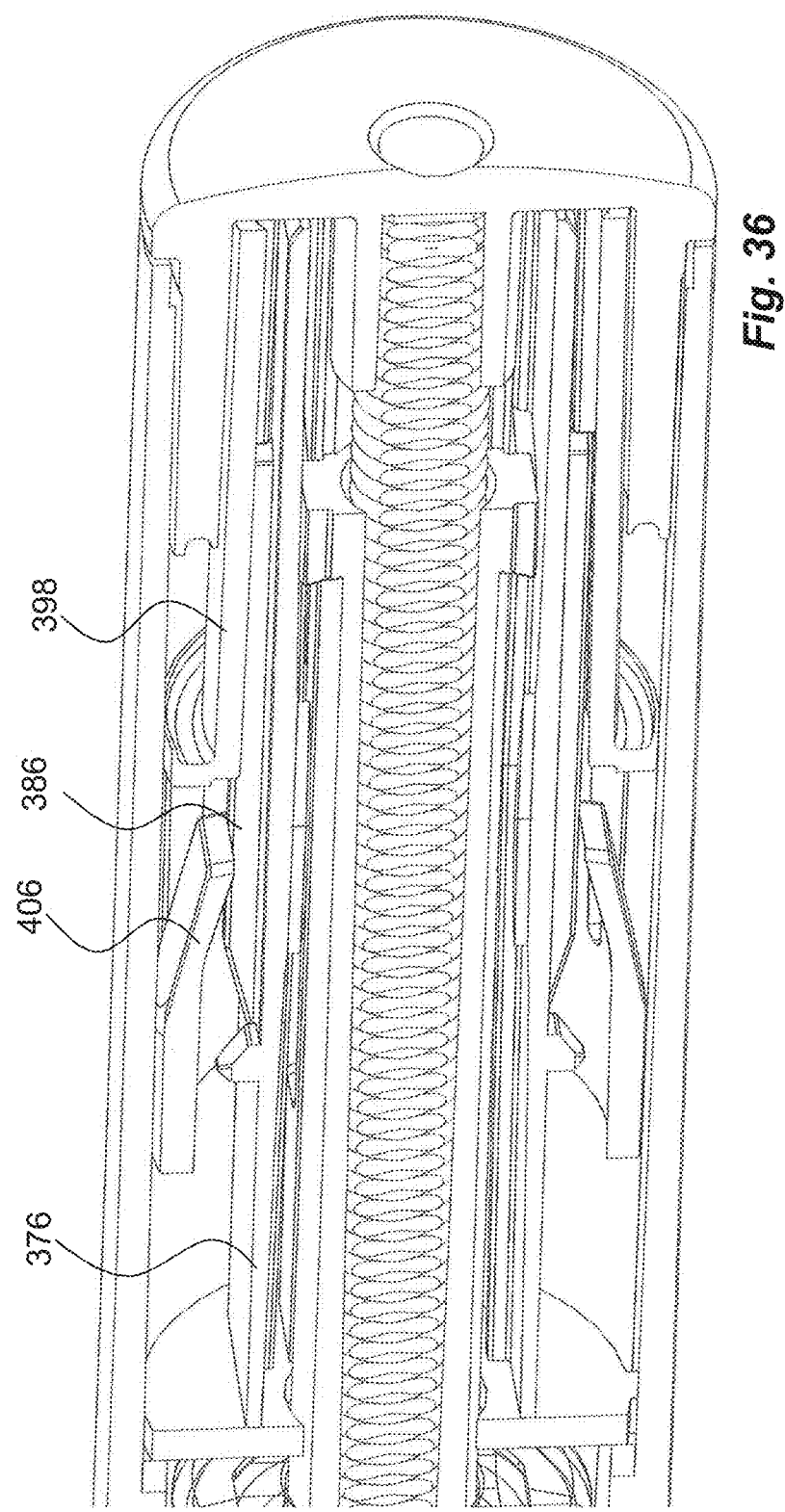
Figure 37:
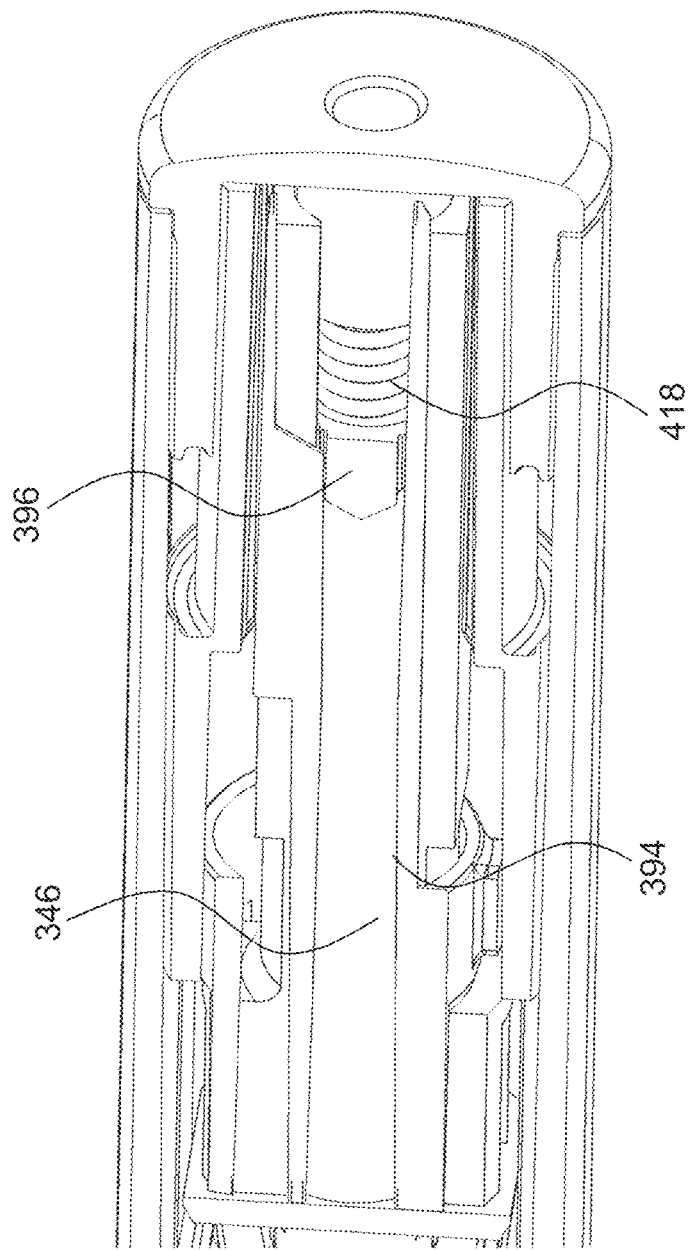
Figure 38:
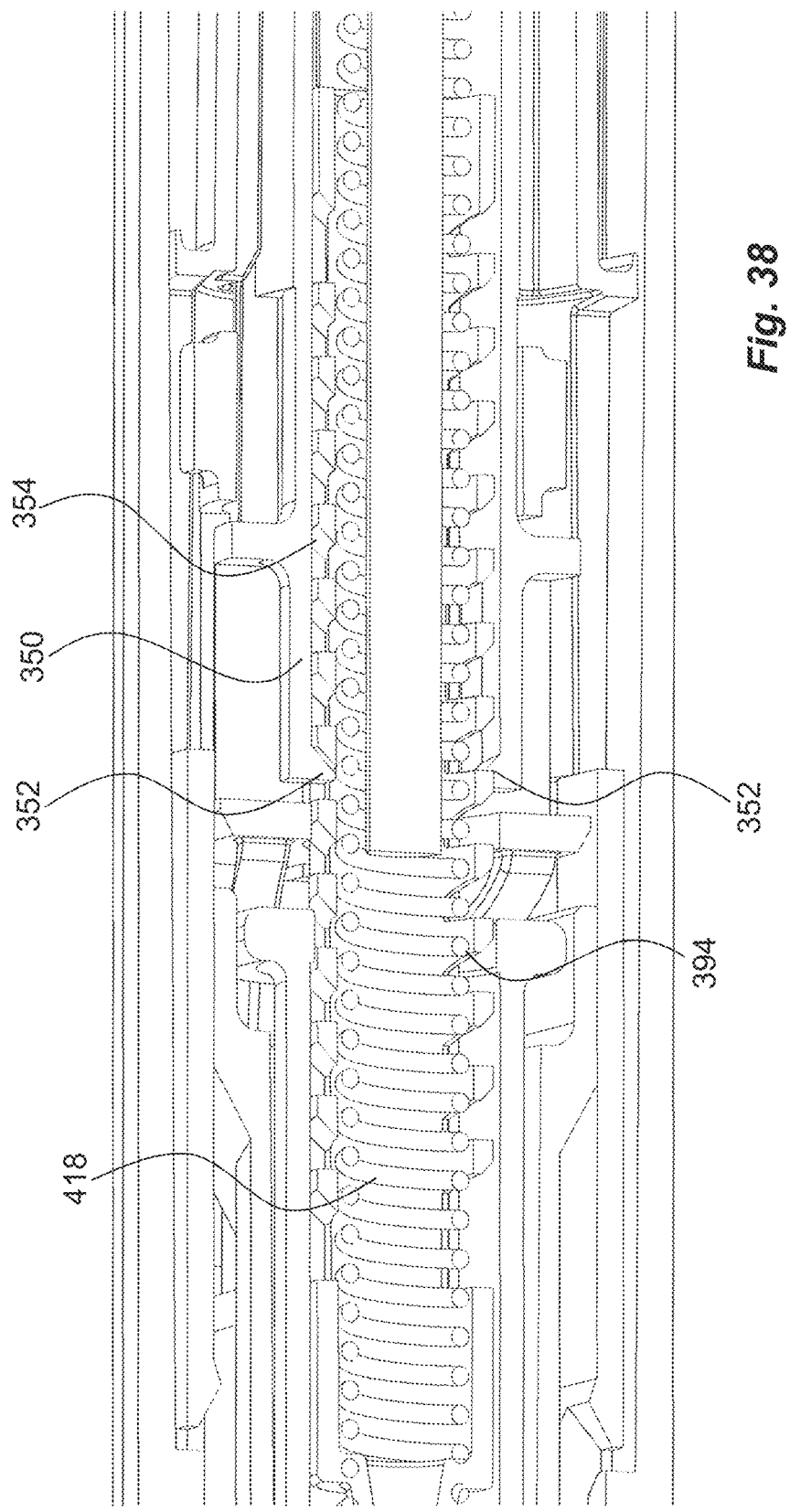
Figure 39:
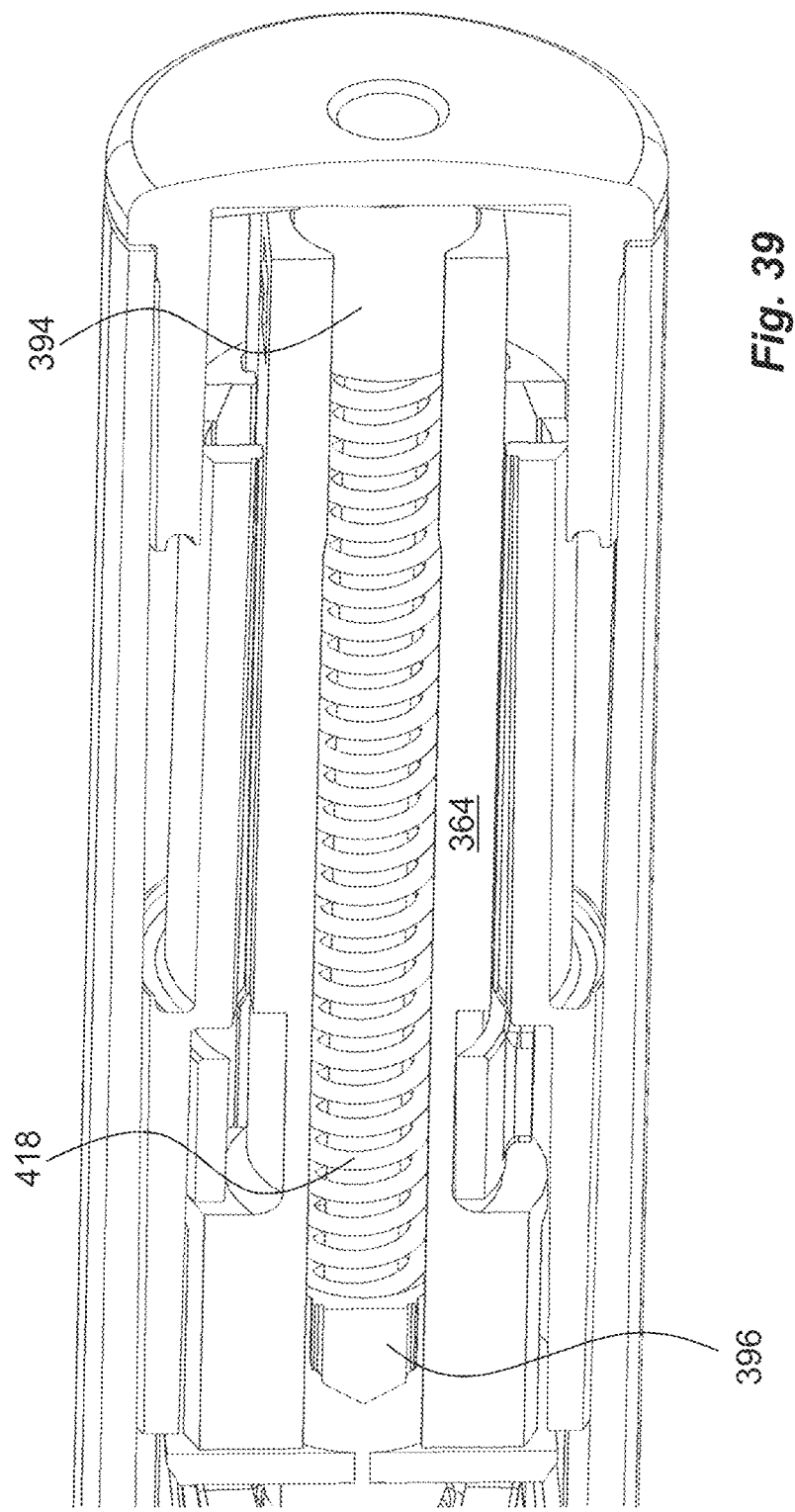

The function of the second embodiment is largely the same as for the first embodiment. The power pack 328 is assembled much in the same way as the previous embodiment with the difference that now the end cap 364 locks the power pack 328 to the housing 300 via its outwardly directed protrusions 372 fitting into the cut-outs 374 of the distal part of the housing 300. When delivered to a user the plunger rod 346 is held with the drive spring 418 in a tensioned state by the protrusions 396 of the plunger rod 346 resting on the inclined ledges of the slider, FIG. 33. As seen in FIG. 34 the contact surfaces of the protrusions 396 and the inclined support surfaces 392 have a certain undercut, ensuring a firm connection. The slider 376 is prevented from moving by the guide ledges of the lock sleeve 398 being in contact with the ledges of the slider 376. When a medicament delivery device is to be used after an end cap 430 has been removed, the proximal end is pressed against a dose delivery site, whereby a medicament delivery member guard 432 is moved distally in relation to the housing. This movement also affects the lock sleeve 398 so that it is moved distally in relation to the slider 376, whereby the guide ledges 414 of the lock sleeve 398 slide along the ledges 386 of the slider 376, FIG. 35. During this movement, the inclined tongues 406 of the lock sleeve 398 will enter the bevelled surfaces 388 and climb up on the outer surface of the ledges 386 of the slider 376, FIG. 36, which will have a stabilizing effect on the slider 376 for the during the movement of the lock sleeve 398. As with the previous embodiment, the slider 376 will be released when the guide ledges 414 of the lock sleeve 398 are moved out of contact with the ledges 386 of the slider 376, whereby the force from the drive spring 418 will cause the plunger rod 346 to be urged in the proximal direction and applying a force on the inclined support surfaces 392 of the slider 376 by its protrusions 396 such that the distal end of the slider 376 is moved in a generally transversal direction until the protrusions 396 enter the longitudinal grooves 394 of the slider 376, FIG. 37, wherein the movement of the slider 376 is facilitated by the slightly curved shape of its proximal end surface 380.

The plunger rod 346 is now free to move in the proximal direction by the drive spring 418, in turn moving a stopper 434 of the medicament container 318 such that a dose of medicament is delivered at the dose delivery site. During the movement of the plunger rod 346, its protrusions will move the slider 376 in the transversal direction. Further, during the movement of the plunger rod 346, the signalling elements 348 will cause a continuous sound in that the ledges 352 of the tongues 350 of the plunger rod holder 330 will be contacting the protrusions/recesses 354 of the plunger rod 346, FIG. 38. This signalling will stop when the plunger rod 346 has reached its most proximal position, FIG. 39, indicating to the user that it is safe to remove the medicament delivery device. When doing so, the medicament delivery member guard 54 will extend in the proximal direction by the force of the lock sleeve spring 200, thus also moving the lock sleeve 398 in the proximal direction. During this movement, the stop surfaces 408 at the ends of the tongues 406 of the lock sleeve 398 will pass the stop ledge 389 of the slider 376, FIG. 40, at a position when the medicament delivery member guard 54 is covering a medicament delivery member 436, which will prevent any movement in the distal direction of the medicament delivery member guard 432, in turn preventing any accidental injuries by the medicament delivery member 436. The medicament delivery device may now be discarded in a safe way.

It should be understood that the medicament delivery device described above and shown in the drawings is to be regarded only as a non-limiting example and that it may be modified in many way within the scope of the patent claims.

The invention claimed is:

1. A drive unit for a medicament delivery device, the drive unit comprising:
   an elongated plunger rod extending in a longitudinal direction, where the plunger rod comprises a plurality of sound or vibration elements on an outer surface and a co-acting element at a distal end of the elongated plunger rod and where the elongated plunger rod is hollow and has an open distal end and a closed proximal end;
   a plunger rod holder comprising a beam positioned transverse to the longitudinal direction, where the beam sequentially contacts individual sound or vibration elements of the plurality of sound or vibration elements when the elongated plunger rod moves axially and proximally relative to the plunger rod holder;

a drive force element capable of applying a drive force on the elongated plunger rod, where a proximal end of the drive force element is positioned within the elongated plunger rod;

an actuator operably connected to the co-acting element on the elongated plunger rod for releasably holding the elongated plunger rod in an energized state when the drive force element is exerting the drive force on the elongated plunger rod;

an activator operably connected to the actuator for releasably holding the actuator in a holding position, where axial movement of the activator causes the actuator to move from the holding position when the co-acting element on the elongated plunger rod forces a distal portion of the actuator to move in a direction generally transversal to the longitudinal direction resulting in the axial and proximal displacement of the elongated plunger rod.

2. The drive unit according to claim 1, wherein the co-acting element is configured to interact with a corresponding co-acting element on the actuator, and wherein the actuator is movable in a direction generally transversal to the longitudinal direction between a holding position in which the co-acting element and the corresponding co-acting element interact with each other for releasably holding the elongated plunger rod in the energized state and a release position in which the co-acting element and the corresponding co-acting element no longer interact with each other such that the elongated plunger rod is released from the energized state.

3. The drive unit according to claim 2, wherein the co-acting element is a radial extending protrusion and the corresponding co-acting element is a stop ledge.

4. The drive unit according to claim 3, wherein the stop ledge has an inclination in relation to the longitudinal direction such that the force from an energized drive force element acting on the elongated plunger rod allows the radial extending protrusion to slide along the stop ledge whereby the actuator is forced to move from the holding position to the release position upon a longitudinal movement of the activator.

5. The drive unit according to claim 4, wherein the actuator further is arranged with a guide element interacting with the protrusion on the elongated plunger rod.

6. The drive unit according to claim 2, wherein the actuator is held in the holding position by the activator.

7. The drive unit according to claim 6, wherein the activator is arranged slidable in the longitudinal direction in relation to the actuator between a first position blocking the actuator and a second position unblocking the actuator.

8. The drive unit according to claim 7, wherein the activator is arranged with guide surfaces configured to cooperate with guide surfaces of the actuator until the second position is reached by the activator.

9. The drive unit according to claim 8, further comprising an end cap fixedly connected to the plunger rod holder that is generally surrounding and guiding the elongated plunger rod and an activator spring arranged between the end cap and the activator.

10. The drive unit according to claim 9, where the plurality of sound or vibration elements on the elongated plunger rod is arranged to interact with the beam on the plunger rod holder for providing audible and tactile information during the proximal axial movement of the elongated plunger rod relative to the plunger rod holder.

11. The drive unit according to claim 1, wherein the activator further comprises a locking element and the actuator further comprises a counter locking member; wherein the counter locking member is axially misaligned with the locking element when the actuator is in the holding position; wherein the counter locking member is axially aligned with the locking element when the actuator is transversally moved out from the holding position.

12. The drive unit according to claim 11, wherein the locking element is configured to interact with the counter locking member in a lockout position, such that a distal axial movement of the activator in relation to the drive unit is prevented.

13. The drive unit according to claim 11, wherein the locking element comprises a flexible tongue with an inward directed protrusion arranged on an inner surface of the flexible tongue.

14. The drive unit according to claim 11, wherein the counter locking member is arranged on an outer surface of the actuator and is transversally movable together with the actuator.

15. A medicament delivery device comprising a drive unit according to claim 1, comprising a housing and a medicament delivery member guard wherein the medicament delivery member guard is slidable between an extended position and a retracted position in relation to the housing and operably connected to the activator such that a sliding movement of the medicament delivery member guard forces the activator to move.

16. The medicament delivery device according to claim 15, further comprising a medicament container holder arranged to accommodate a medicament container, wherein the medicament container holder comprises holding members for releasably holding the medicament container.

17. The medicament delivery device according to claim 16, wherein the holding members are arranged resilient for taking up any movement of the medicament container.

18. A drive unit for a medicament delivery device, the drive unit comprising:

an elongated plunger rod extending in a longitudinal direction and comprising a co-acting element at a distal end of the elongated plunger rod, where the elongated plunger rod is hollow and has an open distal end;

a drive force element positioned through the open distal end such that a portion of the drive force element is located within the hollow elongated plunger rod to apply a drive force on a proximal end of the elongated plunger rod;

an actuator operably connected to the elongated plunger rod for releasably holding the elongated plunger rod in an energized state when the drive force element is exerting the drive force on the elongated plunger rod;

an activator operably connected to the actuator for releasably holding the actuator in a holding position, where axial movement of the activator causes the actuator to move from the holding position when the co-acting element on the elongated plunger rod forces a distal portion of the actuator to move in a direction generally transversal to the longitudinal direction resulting in axial and proximal displacement of the elongated plunger rod.

* * * * *